US010430550B2

United States Patent
Backhaus et al.

(10) Patent No.: US 10,430,550 B2
(45) Date of Patent: *Oct. 1, 2019

(54) MEDICAL IMAGE METADATA PROCESSING

(71) Applicant: Virtual Radiologic Corporation, Minneapolis, MN (US)

(72) Inventors: Brent Backhaus, Crosslake, MN (US); Lorna Backhaus, Crosslake, MN (US); Dean Ebesu, San Francisco, CA (US); Tom J. Gleeson, Dekalb, IL (US); Deke Weinblatt, Otsego, MN (US)

(73) Assignee: Virtual Radiologic Corporation, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/079,284

(22) Filed: Nov. 13, 2013

(65) Prior Publication Data
US 2014/0142983 A1 May 22, 2014

Related U.S. Application Data

(63) Continuation of application No. 13/423,513, filed on Mar. 19, 2012, now Pat. No. 8,612,253, which is a (Continued)

(51) Int. Cl.
*G16H 40/20* (2018.01)
*G06F 19/00* (2018.01)
(Continued)

(52) U.S. Cl.
CPC .......... *G06F 19/321* (2013.01); *G06Q 10/06* (2013.01); *G06Q 50/22* (2013.01); *G16H 40/20* (2018.01)

(58) Field of Classification Search
CPC .................................................. G16H 40/20
(Continued)

(56) References Cited

U.S. PATENT DOCUMENTS

| 3,995,106 A | 11/1976 | Wern et al. |
| 4,003,023 A | 1/1977 | Benson et al. |
| 4,058,835 A | 11/1977 | Kennedy |
| 4,261,018 A | 4/1981 | Knowlton |

(Continued)

FOREIGN PATENT DOCUMENTS

| WO | WO-01/99407 A1 | 12/2001 |
| WO | WO-2005/006138 A2 | 1/2005 |

(Continued)

OTHER PUBLICATIONS

"U.S. Appl. No. 13/333,767, Notice of Allowance dated Aug. 22, 2013", 12 pgs.

(Continued)

*Primary Examiner* — John A Pauls
(74) *Attorney, Agent, or Firm* — Schwegman Lundberg & Woessner, P.A.

(57) ABSTRACT

Enhanced techniques for the extraction and use of metadata from medical images are disclosed herein. Based on the information in the metadata, specific processing may be performed within an image order management system, radiology information system (RIS), or like system. A radiology read order may be created, pre-populated, and transmitted via a processing system (e.g., a teleradiology image order management system) based on the metadata within the radiology image. For example, this metadata may exist within the header of a DICOM-formatted image data file or a DICOM communication protocol transmission. The processing system may then provide the prepopulated read order back to the source of the medical images for verification and submission. Other processing actions may also occur based on information extracted from the image metadata, such as custom workflows and handling based on an originating facility, or transferring the images to a particular radiologist or location.

23 Claims, 4 Drawing Sheets

Related U.S. Application Data continuation of application No. 12/856,096, filed on Aug. 13, 2010, now Pat. No. 8,145,503, which is a continuation-in-part of application No. 12/783,073, filed on May 19, 2010, now Pat. No. 7,925,521, which is a continuation of application No. 11/288,645, filed on Nov. 28, 2005, now Pat. No. 7,729,928.

(60) Provisional application No. 60/740,454, filed on Nov. 28, 2005, provisional application No. 60/740,527, filed on Nov. 28, 2005, provisional application No. 60/740,589, filed on Nov. 28, 2005, provisional application No. 60/699,119, filed on Jul. 14, 2005, provisional application No. 60/694,880, filed on Jun. 29, 2005, provisional application No. 60/682,052, filed on May 17, 2005, provisional application No. 60/656,215, filed on Feb. 25, 2005.

(51) Int. Cl.
  *G06Q 10/06* (2012.01)
  *G06Q 50/22* (2018.01)

(58) Field of Classification Search
  USPC .............................................. 705/2; 382/131
  See application file for complete search history.

(56) References Cited

U.S. PATENT DOCUMENTS

| | | |
|---|---|---|
| 4,302,775 A | 11/1981 | Widergren et al. |
| 4,458,267 A | 7/1984 | Dolazza |
| 4,463,386 A | 7/1984 | Goddard et al. |
| 4,541,012 A | 9/1985 | Tescher |
| 4,604,653 A | 8/1986 | Shimizu |
| 4,614,978 A | 9/1986 | Doster et al. |
| 4,622,585 A | 11/1986 | Reitsma |
| 4,631,521 A | 12/1986 | El-sherbini |
| 4,652,933 A | 3/1987 | Koshiishi |
| 4,748,511 A | 5/1988 | Nicols et al. |
| 4,764,870 A | 8/1988 | Haskin |
| 4,860,112 A | 8/1989 | Nichols et al. |
| 4,910,609 A | 3/1990 | Nicholas et al. |
| 5,216,596 A | 6/1993 | Weinstein et al. |
| 5,291,401 A | 3/1994 | Robinson |
| 5,321,520 A | 6/1994 | Inga et al. |
| 5,416,602 A | 5/1995 | Inga et al. |
| 5,452,416 A | 9/1995 | Hilton et al. |
| 5,469,353 A | 11/1995 | Pinsky et al. |
| 5,469,535 A | 11/1995 | Jarvis et al. |
| 5,513,101 A | 4/1996 | Pinsky et al. |
| 5,631,953 A | 5/1997 | Thomas et al. |
| 5,655,084 A | 8/1997 | Pinsky et al. |
| 6,006,191 A | 12/1999 | DiRienzo |
| 6,035,276 A | 3/2000 | Newman et al. |
| 6,115,486 A | 9/2000 | Cantoni |
| 6,137,527 A | 10/2000 | Abdel-malek et al. |
| 6,272,470 B1 | 8/2001 | Teshima |
| 6,302,844 B1 | 10/2001 | Walker et al. |
| 6,314,452 B1 | 11/2001 | Dekel et al. |
| 6,381,029 B1 | 4/2002 | Tipirneni |
| 6,424,996 B1 | 7/2002 | Killcommons et al. |
| 6,448,956 B1 | 9/2002 | Berman et al. |
| 6,473,524 B1 | 10/2002 | Reda et al. |
| 6,481,887 B1 | 11/2002 | Mirabella |
| 6,571,214 B2 | 5/2003 | Newman et al. |
| 6,574,629 B1 | 6/2003 | Cook, Jr. et al. |
| 6,603,494 B1 | 8/2003 | Banks et al. |
| 6,621,918 B1 | 9/2003 | Hu et al. |
| 6,625,252 B2 | 9/2003 | Mirabella |
| 6,678,703 B2 | 1/2004 | Rothschild et al. |
| 6,798,533 B2 | 9/2004 | Tipirneni |
| 6,820,057 B1 | 11/2004 | Loch et al. |
| 6,876,759 B2 | 4/2005 | Keller et al. |
| 6,915,266 B1 | 7/2005 | Saeed et al. |
| 7,136,883 B2 | 11/2006 | Flamma et al. |
| 7,500,185 B2 | 3/2009 | Hu |
| 7,562,026 B2 | 7/2009 | DelMonego et al. |
| 7,729,928 B2 | 6/2010 | Backhaus et al. |
| 7,756,724 B2 | 7/2010 | Gropper et al. |
| 7,925,521 B2 | 4/2011 | Backhaus et al. |
| 7,970,634 B2 | 6/2011 | Backhaus et al. |
| 8,090,593 B2 | 1/2012 | Backhaus et al. |
| 8,145,503 B2 | 3/2012 | Backhaus et al. |
| 8,195,481 B2 | 6/2012 | Backhaus |
| 8,229,761 B2 | 7/2012 | Backhaus et al. |
| 8,515,778 B2 | 8/2013 | Backhaus |
| 8,612,250 B2 | 12/2013 | Backhaus et al. |
| 8,612,253 B2 | 12/2013 | Backhaus et al. |
| 2001/0032215 A1 | 10/2001 | Kyle et al. |
| 2001/0041991 A1 | 11/2001 | Segal et al. |
| 2002/0016718 A1 | 2/2002 | Rothschild et al. |
| 2002/0019751 A1 | 2/2002 | Rothschild et al. |
| 2002/0065758 A1 | 5/2002 | Henley |
| 2002/0087503 A1 | 7/2002 | Judd et al. |
| 2002/0102012 A1 | 8/2002 | Keller et al. |
| 2002/0102028 A1 | 8/2002 | Keller et al. |
| 2002/0109859 A1 | 8/2002 | Tipirneni |
| 2002/0161605 A1 | 10/2002 | Newman et al. |
| 2002/0169637 A1 | 11/2002 | Akers et al. |
| 2002/0198454 A1 | 12/2002 | Seward et al. |
| 2003/0004409 A1 | 1/2003 | Mueller et al. |
| 2003/0061090 A1 | 3/2003 | Marano |
| 2003/0086595 A1 | 5/2003 | Hu et al. |
| 2003/0126148 A1* | 7/2003 | Gropper ................ G06F 19/327 |
| 2003/0149598 A1 | 8/2003 | Santoso et al. |
| 2004/0064343 A1 | 4/2004 | Korpman et al. |
| 2004/0117617 A1 | 6/2004 | Geller et al. |
| 2004/0167402 A1 | 8/2004 | Jones et al. |
| 2004/0186764 A1 | 9/2004 | Mcneill |
| 2004/0254822 A1 | 12/2004 | Mandelbaum |
| 2004/0257608 A1 | 12/2004 | Tipirneni |
| 2005/0002483 A1 | 1/2005 | Wilcox, Jr. |
| 2005/0021375 A1 | 1/2005 | Shimizu et al. |
| 2005/0075902 A1 | 4/2005 | Wager et al. |
| 2005/0101856 A1 | 5/2005 | Judd et al. |
| 2005/0114380 A1 | 5/2005 | Eldar et al. |
| 2005/0234741 A1 | 10/2005 | Rana et al. |
| 2006/0053035 A1 | 3/2006 | Eisenberg |
| 2006/0095423 A1 | 5/2006 | Reicher et al. |
| 2006/0168338 A1 | 7/2006 | Bruegl et al. |
| 2006/0195339 A1 | 8/2006 | Backhaus et al. |
| 2007/0005798 A1 | 1/2007 | Gropper et al. |
| 2007/0073556 A1 | 3/2007 | Lau et al. |
| 2009/0089092 A1 | 4/2009 | Johnson et al. |
| 2009/0198559 A1 | 8/2009 | Wang et al. |
| 2009/0327049 A1 | 12/2009 | Kisin et al. |
| 2010/0198609 A1 | 8/2010 | Mellin et al. |
| 2010/0256986 A1 | 10/2010 | Backhaus et al. |
| 2011/0004490 A1 | 1/2011 | Backhaus et al. |
| 2011/0010192 A1 | 1/2011 | Backhaus et al. |
| 2011/0015941 A1 | 1/2011 | Backhaus |
| 2011/0066449 A1 | 3/2011 | Backhaus et al. |
| 2011/0191118 A1 | 8/2011 | Backhaus et al. |
| 2012/0245949 A1 | 9/2012 | Backhaus et al. |
| 2012/0265551 A1 | 10/2012 | Backhaus et al. |
| 2012/0323593 A1 | 12/2012 | Backhaus |
| 2013/0066646 A1 | 3/2013 | Backhaus et al. |
| 2014/0088987 A1 | 3/2014 | Backhaus |
| 2014/0142969 A1 | 5/2014 | Backhaus et al. |

FOREIGN PATENT DOCUMENTS

| | | |
|---|---|---|
| WO | WO-2006/093544 A2 | 9/2006 |
| WO | WO-2006093544 A2 | 9/2006 |
| WO | WO-2010/087911 A1 | 8/2010 |
| WO | WO-2012/064819 A1 | 5/2012 |

OTHER PUBLICATIONS

"U.S. Appl. No. 13/333,767, Response filed Jul. 18, 2013 to Non Final Office Action dated Mar. 20, 2013", 15 pgs.

(56) References Cited

OTHER PUBLICATIONS

"U.S. Appl. No. 13/423,513, Non Final Office Action dated Mar. 19, 2013", 16 pgs.
"U.S. Appl. No. 13/423,513, Notice of Allowance dated Aug. 20, 2013", 11 pgs.
"U.S. Appl. No. 13/423,513, Response filed Jul. 18, 2013 to Non Final Office Action dated Mar. 19, 2013", 16 pgs.
"U.S. Appl. No. 13/423,513, Supplemental Notice of Allowability dated Oct. 10, 2013", 5 pgs.
"Canadian Application Serial No. 2,636,705, Office Action dated Mar. 12, 2014", 3 pgs.
"Defendants' Supplemental Prior Art Statement dated Apr. 11, 2014", *Virtual Radiologic Corporation, et al. v. Tandem Radiology, LLC, et al.*, (Civil Action No. 2:13-cv-01705-DKD, United States District Court for the District of Arizona), 27 pgs.
"EX. A—Defendant Tandem Radiology's proposed Prior Art Contentions Chart for U.S. Pat. No. 8,195,481", (Apr. 11, 2014), 140 pgs.
"EX. B—Defendant Tandem Radiology's proposed Prior Art Contentions Chart for U.S. Pat. No. 7,970,634", (Apr. 11, 2014), 182 pgs.
"EX. C—Defendant Tandem Radiology's proposed Prior Art Contentions Chart for U.S. Pat. No. 8,145,503", (Apr. 11, 2014), 285 pgs.
"EX. D—Defendant Tandem Radiology's proposed Prior Art Contentions Chart for U.S. Pat. No. 8,090,593", (Apr. 11, 2014), 132 pgs.
"EX. E—Defendant Tandem Radiology's proposed Prior Art Contentions Chart for U.S. Pat. No. 8,515,778", (Apr. 11, 2014), 115 pgs.
"MGRIS—Global Radiology Information System", Medweb(r), (before Nov. 2013), 1 pg.
"RIS Logic Module Workflow Functionality Highlights", [online]. [archived on Jan. 5, 2004]. Retrieved from the Internet: <URL: http://web.archive.org/web/20040105160056/http://www.merge.com/products/pacsteleradiologyweb/rislogiccs_features.asp>, (2004), 6 pgs.
"State Telemedicine Licensure as of Jul. 15, 2001", [online]. © 1994-2002 American College of Radiology. [archived on Sep. 17, 2002]. Retrieved from the Internet: <URL: http://web.archive.org/web/20020917202928/http://www.acr.org/cgi-bin/fr?mast:mastheaddepartments,text/departments/govt_rel/text.html>, (Revised Feb. 2002), 7 pgs.
"ThinAir Data", Promotional Material, (before Nov. 2013), 2 pgs.
"ThinAir Data—SkyRIS DR—Bringing Speech, Wireless & Internet Technologies to Healthcare", [online]. [archived on Jun. 7, 2001], Retrieved from the Internet: <URL: http://web.archive.org/web/20010607094324/http://thinairdata.com/SkyRIS/DR/dr.html>, (2001), 1 pg.
"ThinAir Data—SkyRIS—Speech, Wireless and the Internet—Healthcare at the speed of thought", (before Nov., 2013), 2 pgs.
"ThinAir Data—SkyRIS Teleradiology—Speech, Wireless and the Internet—Healthcare at the speed of thought", (before Nov. 2013), 2 pgs.
"ThinAir Data—SkyRIS TeleRIS—Speech, Wireless and the Internet—Healthcare at the speed of thought", (before Nov. 2013), 2 pgs.
Berger, S. B., et al., "Medical-Legal Issues in Teleradiology", *AJR*. 166, (1996), 505-510.
Brice, James, "Globalization comes to radiology", [online]. © 1996-2004 CMP Media LLC. [retrieved on May 22, 2014]. Retrieved from the Internet: <URL: http://web.mit.edu/outsourcing/class1/DIradiology-1.htm>, (Nov. 2003), 7 pgs.
Chacko, Anna K., et al., "Vision and benefits of a virtual radiology environment for the U.S. Army", (Abstract), *Proc. SPIE 3339, Medical Imaging 1998: PACS Design and Evaluation: Engineering and Clinical Issues*, 200, (1998), 2 pgs.
Kalyanpur, Arjun, et al., "Implementation of an International Teleradiology Staffing Model", Radiology, 232(2), (Aug. 2004), 415-419.
Martinez, Ralph, et al., "Virtual Management of Radiology Examinations in the Virtual Radiology Environment Using Common Object Request Broker Architecture Services", *Journal of Digital Imaging*, 12(2)(Suppl. 1), (1999), 181-185.
Mun, Seong G., et al., "Teleradiology and emerging business models", *J. Telemed. Telecare*, 11(6), (2005), 271-275.
Siegel, Eliot, et al., "Work Flow Redesign: The Key to Success When Using PACS", *AJR*, 178 (Mar. 2002), 563-566.
"14-Step RIS/PACS Selection Process", [Online]. [Archived Apr. 27, 2004]. Retrieved from the Internet: <URL: http://web.archive.org/web/20040427134813/http://www.merge.com/pdf/14%20Step%20RIS-PACS%20Selection%20Process.pdf>, 2 pgs.
"All-In-One Server", [Online]. [Archived Jul. 15, 2004]. Retrieved from the Internet: <URL: http://web.archive.org/web/20040715234715/http://www.medweb.com/all_in_one.pdf >, 4 pgs.
"U.S. Appl. No. 13/084,379, Preliminary Amendment dated Jun. 30, 2011", 14 pgs.
"U.S. Appl. No. 13/084,379, Preliminary Amendment dated Oct. 21, 2011", 16 pgs.
"U.S. Appl. No. 13/449,004, Preliminary Amendment dated Apr. 17, 2012", 3 pgs.
"U.S. Appl. No. 13/449,004, Preliminary Amendment dated Sep. 12, 2012", 10 pgs.
"U.S. Appl. No. 13/550,319, Notice of Allowance dated Jun. 26, 2014", 11 pgs.
"U.S. Appl. No. 13/550,319, Preliminary Amendment dated Jun. 16, 2014", 10 pgs.
"U.S. Appl. No. 13/550,319, Preliminary Amendment dated Jul. 16, 2012", 3 pgs.
"U.S. Appl. No. 13/550,319, Preliminary Amendment dated Nov. 30, 2012", 6 pgs.
"U.S. Appl. No. 13/550,319, Preliminary Amendment dated Dec. 21, 2012", 9 pgs.
"U.S. Appl. No. 13/966,594, Preliminary Amendment dated Aug. 14, 2013", 3 pgs.
"Building Referrals Through Internet Gateways", [Online]. [Archived Dec. 13, 2004]. Retrieved from the Internet: <URL: http://web.archive.org/web/20041213164514/http://www.merge.com/pdf/Internet%20Gateways%20White%20Paper.pdf>, 8 pgs.
"Canadian Application Serial No. 2,636,705, Office Action dated Jul. 17, 2012", 4 pgs.
"Canadian Application Serial No. 2,636,705, Response filed Sep. 11, 2014 to Office Action dated Mar. 12, 2014", 4 pgs.
"Canadian Application Serial No. 2,636,705, Response filed Dec. 18, 2012 to Office Action dated Jul. 17, 2012", 14 pgs.
"Compact Conversion Device for Non-DICOM Modalities", [Online]. [Archived May 17, 2000]. Retrieved from the Internet: <URL: http://web.archive.org/web/20000517131011/http://www.medweb.net/html/dicomizer.html >, 1 pg.
"Complete teleradiology reporting and distribution workflow solution", [Online]. [Archived May 31, 2004]. Retrieved from the Internet: <URL: http://web.archive.org/web/20040531042632/http://www.thinairdata.com/docs/SkyRISTeleradiology.pdf >, 2 pgs.
"Complete workflow, reporting and distribution solution for multi-contract radiology and teleradiology", [Online]. [Archived Nov. 12, 2004]. Retrieved from the Internet: <URL: http://web.archive.org/web/20041112122403/http://www.thinairdata.com/docs/ThinAirData_TeleRIS.pdf >, 2 pgs.
"Defendants' 2nd Amended Prior Art Statement", *Virtual Radiologic Corporation, et al. v. Tandem Radiology, LLC, et al.*,, Civil Action No. 2:13-cv-01705-DKD, United States District Court for the District of Arizona, (Aug. 18, 2014), 19 pgs.
"DICOM Cube", [Online]. [Archived Feb. 19, 1999. Retrieved from the Internet: <URL: http://web.archive.org/web/19990219213946/http://www.medweb.com/html/dicom_cube.html>, 1 pg.
"DICOM Cube, Raq3, Raq4 Mixed Input Clinical Webservers", [Online]. Retrieved from the Internet: <URL: http://web.archive.org/web/20040206094442/http://www.medweb.com/Mixed_Input_Webservers.pdf >, (2002), 4 pgs.
"Dictation, Transcription and Practice Management", [Online]. [Archived Jul. 16, 2004]. Retrieved from the Internet: <URL: http://web.archive.org/web/20040716024128/http://www.medweb.com/Dictation_Transcription.pdf >, 2 pgs.

(56) References Cited

OTHER PUBLICATIONS

"Digital Publisher Gateway", [Online]. [Archived Jul. 3, 2003]. Retrieved from the Internet: <URL: http://web.archive.org/web/20030703020011/http://www.medweb.com/CD_spec_sheet.pdf>, 2 pgs.
"European Application Serial No. 05852463.8, Search Report dated Feb. 24, 2010", 6 pgs.
"Full feature RIS with integrated speech recognition and transcription", [Online]. [Archived Jun. 9, 2003]. Retrieved from the Internet: <URL: http://web.archive.org/web/20030609085309/http://thinairdata.com/docs/SkyRIS.pdf >, 2 pgs.
"Full feature RIS with integrated speech recognition and transcription", [Online]. [Archived Jul. 27, 2004]. Retrieved from the Internet: <URL: http://web.archive.org/web/20040727053227/http://www.thinairdata.com/docs/SkyRIS.pdf >, 2 pgs.
"Fusion RIS/PACS: Intelligent, Distributed Workflow", [Online]. [Archived Jun. 16, 2004]. Retrieved from the Internet: <URL: http://web.archive.org/web/20040616013014/http://www.merge.com/products/pacsteleradiologyweb/fusion_rispacs.asp >, 2 pgs.
"Improving Profitability with E-Document Delivery", [Online]. [Archived Feb. 19, 2004]. Retrieved from the Internet: <URL: http://web.archive.org/web/20040219180157/http://www.merge.com/pdf/Improving%20Profitability%20with%20E-Document%20Delivery.pdf >, 4 pgs.
"Medweb", [Online]. [Archived Apr. 17, 1999]. Retrieved from the Internet: <URL: http://web.archive.org/web/19990417045341/http://www.medweb.com/ >, 1 pg.
"Medweb", [Online]. [Archived Jan. 16, 1998]. Retrieved from the Internet: <URL: http://web.archive.org/web/19980116194946/http://www.medweb.com/ >, 1 pg.
"Medweb", [Online]. [Archived Nov. 11, 1998]. Retrieved from the Internet: <URL: http://web.archive.org/web/19981111184528/http://www.medweb.com/ >, 2 pgs.
"Medweb", [Online]. [Archived Dec. 7, 1998]. Retrieved from the Internet: <URL: http://web.archive.org/web/19981207045132/http://www.medweb.com/ >, 1 pg.
"MEDWEB—Image Server DICOM Conformance Statement Revision 2.1", [Online]. Retrieved from the Internet: <URL: http://web.archive.org/web/20030817102556/http://www.medweb.com/DICOM_Conformance_Image_Server.pdf >, (Jul. 1, 1998), 20 pgs.
"Medweb Browser Plug-Ins", [Online]. [Archived Mar. 2, 2000]. Retrieved from the Internet: <URL: http://web.archive.org/web/20000302082914/http://www.medweb.com/html/plug-ins.html >, 2 pgs.
"Medweb Image Viewer Plugin", [Online]. [Archived Apr. 14, 2003]. Retrieved from the Internet: <URL: http://web.archive.org/web/20030414183706/http://medweb.com/html/plug-ins.html >, 2 pgs.
"Medweb Introduced Breakthrough Web-based Enterprise Telemedicine Solution", [Online]. [Archived Mar. 2, 2000]. Retrieved from the Internet: <URL: http://web.archive.org/web/20000302143424/http://www.medweb.com/html/pr-ets.html >, 2 pgs.
"Medweb Introduces Breakthrough Web-based Enterprise Telemedicine Solution", [Online]. [Archived Apr. 8, 2000]. Retrieved from the Internet: <URL: http://web.archive.org/web/20000408232851/http://www.medweb.net/html/t-server.html >, 2 pgs.
"Medweb Introduces New TELEMED Cube Bi-Directional Telemedicine Server", [Online]. [Archived Apr. 8, 2001]. Retrieved from the Internet: <URL: http://web.archive.org/web/20010408055000/http://www.medweb.com/html/t-cube.html >, 2 pgs.
"Medweb Introduces the DICOM Cube, Complete Web-Based Solution for Distribution of DICOM Studies", [Online]. [Archived Mar. 2, 2000]. Retrieved from the Internet: <URL: http://web.archive.org/web/20000302122612/http://www.medweb.com/html/pr-dcube.html >, 3 pgs.
"Medweb PDA Gateway", [Online]. [Archived Jul. 16, 2004]. Retrieved from the Internet: <URL: http://web.archive.org/web/20040716045513/http://www.medweb.com/pda_Gateway.pdf>, 1 pg.

"Medweb RIS With Integrated Web Scheduler", [Online]. [Archived Jul. 16, 2004]. Retrieved from the Internet: <URL: http://web.archive.org/web/20040716023259/http://www.medweb.com/RIS.pdf >, 2 pgs.
"Merge Radiology Solutions", [Online]. Retrieved from the Internet: <URL: http://www.merge.com/Solutions/Radiology.aspx>, (Accessed Oct. 31, 2014), 4 pgs.
"MGRIS—Global Radiology Information System", [Online]. [Archived Oct. 22, 2004]. Retrieved from the Internet: <URL: http://web.archive.org/web/20041022044754/http://www.medweb.com/mgris_pdf.pdf>, 1 pg.
"MGRIS—Global Radiology Information System", [Online]. [Archived Jul. 16, 2004]. Retrieved from the Internet: <URL: http://web.archive.org/web/20040716030818/http://www.medweb.com/mgris_pdf.pdf >, 1 pg.
"Pacsguardian", [Online]. [Archived Jul. 16, 2004]. Retrieved from the Internet: <URL: http://web.archive.org/web/20040716013608/http://www.medweb.com/pacsguardian_pdf.pdf >, 2 pgs.
"Practice Analysis—Converting Data to Profits", [Online]. [Archived Feb. 19, 2004]. Retrieved from the Internet: <URL: http://web.archive.org/web/20040219151236/http://www.merge.com/pdf/Practice%20Analysis%20White%20Paper.pdf >, 11 pgs.
"Radiologist Dashboard", [Online]. [Archived May 12, 2005]. Retrieved from the Internet: <URL: http://web.archive.org/web/20050512075349/http://www.medweb.com/Dashboard.pdf >, 2 pgs.
"RIS Logic Module Features", [Online]. [Archived Jan. 5, 2004]. Retrieved from the Internet: <URL: http://web.archive.org/web/20040105160056/http://www.merge.com/products/pacsteleradiologyweb/rislogiccs_features.asp>, 6 pgs.
"SkyRIS DR", [Online]. [Archived Jun. 7, 2001]. Retrieved from the Internet: <URL: http://web.archive.org/web/20010607094324/http://thinairdata.com/SkyRIS/DR/dr.html >, 1 pg.
"Smart Monitor: Multi-Site monitoring software for remote radiology reading services and distributed failsafe, secure, reading networks", [Online]. [Archived Jul. 16, 2004]. Retrieved from the Internet: <URL: http://web.archive.org/web/20040716013538/http://www.medweb.com/smart_monitor.pdf >, 2 pgs.
"Survey Documents That a RIS Reduces Turnaround Time by 20%", [Online]. [Archived Feb. 19, 2004]. Retrieved from the Internet: <URL: http://web.archive.org/web/20040219145635/http://www.merge.com/pdf/Turnaround%20Time%20Results.pdf >, 2 pgs.
"Telemed Rack—Medweb Distributed Telemedicine", [Online]. [Archived Jul. 16, 2004]. Retrieved from the Internet: <URL: http://web.archive.org/web/20040716030816/http://www.medweb.com/telemed_brochure.pdf>, 8 pgs.
"TeleRIS is the complete teleradiology workflow, reporting and distribution solution", [Online]. [Archived Oct. 19, 2004]. Retrieved from the Internet: <URL: http://web.archive.org/web/20041019125202/http://thinairdata.com/SkyRISTele.htm >, 3 pgs.
"TeleRIS is the complete teleradiology, multi-contract, multi-facility workflow, reporting and distribution solution", [Online]. [Archived Dec. 9, 2004]. Retrieved from the Internet: <URL: http://web.archive.org/web/20041209091915/http://www.thinairdata.com/SkyRISTele.htm >, 3 pgs.
"The RIS Logic CS Solution—Benefits", [Online]. [Archived Apr. 28, 2004]. Retrieved from the Internet: <URL: http://web.archive.org/web/20040428181757/http://www.merge.com/products/pacsteleradiologyweb/rislogiccs_benefits.asp>, 2 pgs.
"ThinAir Data", [Online]. [Archived Oct. 23, 2006]. Retrieved from the Internet: <URL: http://web.archive.org/web/20061023222251/http://www.thinairdata.com/docs/ThinAir_VRC_Story_030106.pdf>, 2 pgs.
"ThinAir Data—SkyRIS DR", [Online]. [Archived Jun. 7, 2001]. Retrieved from the Internet: <URL: http://web.archive.org/web/20010607094324/http://thinairdata.com/SkyRIS/DR/dr.html >, 1 pg.
"Welcome: ThinAir Data—Healthcare at the Speed of Thought", [Online]. [Archived Nov. 12, 2004]. Retrieved from the Internet: <URL: http://web.archive.org/web/20041112045011/http://www.thinairdata.com >, 2 pgs.
"24/7 Radiology Services", 24/7 Radiology, LLP. [online]. [retrieved on Nov. 2, 2006]. Retrieved from the Internet: <URL: http://www.247rad.com/service.shtml>, (2004), 2 pgs.

(56) References Cited

OTHER PUBLICATIONS

"About HL7", Health Level Seven, [online], [retrieved on Jul. 15, 2005], Retrieved from the Internet: <URL: www.hl7.org/about/about_nav_bar.cfm>, (2005), 15 pgs.

"About IHE", IHE Initiative: ACC/HIMSS/RSNA. [online]. [retrieved on Jul. 15, 2005]. Retrieved from the Internet: <URL: http://www.ihe.net/About/index.cfm>, (2005), 2 pgs.

"About Us!, Emergency Radiology", [online]. [retrieved on Nov. 2, 2006]. Retrieved from the Internet: <URL: http://www.emergencyradiology.net/aboutus.htm>, (2006), 1 pg.

"ACUO Technologies Products, ACUO Technology Product Webpage, Overview and Functionality data for (AcuoMed Image Manager & AcuoStore Digital Asses Manager)", ACUO Technologies, [online]. [retrieved on Nov. 28, 2005]. Retrieved from the Internet: <URL: http://www.acuotech.com/acuoArchive.html>, (2005), 5 pgs.

"ACUO Technology DICOM Archive", ACUO Technologies, LLC. [online]. [retrieved on Nov. 13, 2006], Retrieved from the Internet: <URL: http://www.acuotech.com/acuoArchive.html>, 3 pgs.

"American Radiology offers Images Online to Referring Physicians", American Radiology Services, Inc. [online]. [archived on Feb. 23, 2005]. Retrieved from the Internet: <URL:http://www3.americanradiology.com/pls/web1/wwparticle.viewart?article_id_in=23>, (2003), 1 pg.

"American Radiology Services Nighthawk Services", © 2003 American Radiology Services, Inc. [online]. [retrieved on Nov. 29, 2005]. Retrieved from the Internet: <URL: ]. http://www3.americanradiology.com/pls/web1/wwreadserv.info>, (2003), 2 pgs.

"American Radiology Services Organization Information", © 2003 American Radiology Services. [online]. [retrieved on Feb. 25, 2005], Retrieved from the Internet: <URL: http://www3.americanradiology.com/pls/webllwwaboutars.info >, (2003), 3 pgs.

"American Radiology Services, Inc.—Organization Information", © 2003 American Radiology. [online]. [retrieved on Feb. 25, 2005]. Retrieved from the Internet: <URL: http://www3.americanradiology.com/pls/web1/wwaboutars.info>, (2003), 3 pgs.

"APEX Radiology: A Virtual Radiologist on Staff", Apple Computer, Inc. [online]. [retrieved on Oct. 20, 2006]. Retrieved from the Internet: <URL: http://www.apple.com/science/profiles/apexl >, (2006), 4 pgs.

"U.S. Appl. No. 11/288,645, Non Final Office Action dated Nov. 12, 2009", 20 pgs.

"U.S. Appl. No. 11/288,645, Notice of Allowance dated Mar. 24, 2010", 12 pgs.

"U.S. Appl. No. 11/288,645, Preliminary Amendment dated Mar. 27, 2006", 4 pgs.

"U.S. Appl. No. 11/288,645, Response filed Feb. 12, 2010 to Non Final Office Action dated Nov. 12, 2009", 13 pgs.

"U.S. Appl. No. 12/783,073, Notice of Allowance dated Feb. 22, 2011", 9 pgs.

"U.S. Appl. No. 12/783,073, Preliminary Amendment dated Jan. 10, 2011", 7 pgs.

"U.S. Appl. No. 12/856,096, Notice of Allowance dated Jan. 25, 2012", 14 pgs.

"U.S. Appl. No. 12/856,096, PTO Response to 312 Amendment dated Feb. 27, 2012", 2 pgs.

"U.S. Appl. No. 12/870,271, Notice of Allowance dated Feb. 24, 2012", 9 pgs.

"U.S. Appl. No. 12/882,479, Notice of Allowance dated Mar. 23, 2011", 11 pgs.

"U.S. Appl. No. 12/882,479, Preliminary Amendment dated Jan. 10, 2011", 10 pgs.

"U.S. Appl. No. 12/942,355, Notice of Allowance dated Apr. 12, 2012", 16 pgs.

"U.S. Appl. No. 13/084,379, Notice of Allowance dated Nov. 8, 2011", 13 pgs.

"U.S. Appl. No. 13/333,767, Non Final Office Action dated Mar. 20, 2013", 18 pgs.

"U.S. Appl. No. 13/449,004, Notice of Allowance dated Apr. 22, 2013", 13 pgs.

"U.S. Appl. No. 90/009,889, Examiner Interview Summary dated Jun. 28, 2011", 3 pgs.

"U.S. Appl. No. 90/009,889, Notice of Failure to Comply dated May 6, 2011", 8 pgs.

"U.S. Appl. No. 90/009,889, Order dated Jul. 13, 2011 Denying Request for ex parte Reexmation", 14 pgs.

"U.S. Appl. No. 90/009,889, Petition for Reconsideration filed Aug. 10, 2011", 14 pgs.

"U.S. Appl. No. 90/009,889, Reexam Petition Decision dated Aug. 1, 2012", 15 pgs.

"U.S. Appl. No. 90/009,889, Revised Request for Re-Examination filed May 30, 2011", 10 pgs.

"Benefits", © 2004 Fujifilm UK. [online]. [retrieved on Nov. 28, 2005]. Retrieved from the Internet: <URL: www.fulifilm.co.uk/synapse/about/benefits>, (2004), 3 pgs.

"Cactus Advantage", Cactus Software, [online]. [retrieved on Nov. 2, 2006], Retrieved from the Internet: <URL: http://www.visualcactus.com/Public2002/MCCACTUSAdvantageFull, (2006), 3 pgs.

"Cactus Software Products & Services", [online]. [retrieved on Nov. 2, 2006]. Retrieved from the Internet: <URL: http://www.visualcactus.com/Public2002/HomeFramedPage.htm>, (2006), 1 pg.

"California Radiographics Homepage", California Radiographics Inc. [online]. [retrieved on Sep. 7, 2005]. Retrieved from the Internet: <URL: http://www.nightshiftradiology.com/teleradiology_equipment.htm>, (2005), 4 pgs.

"Cascadable Architecture", © 2004 Fujifilm UK. [online], [retrieved on Nov. 28, 2005]. Retrieved from the Internet: <URL: www.fujifilm.co.uk/synapse/product/cascadable>, (2004), 2 pgs.

"Case Studies EchoApps", © 2006 Healthline Systems Inc. [online]. [retrieved on Nov. 2, 2006]. Retrieved from the Internet: <URL: http://www.healthlinesystems.com/casestudies/echoapps_mc.asp>, (2006), 5 pgs.

"Chatham Radiology Group Deploys Neurostar's Virtual Radiology Network Solution to Improve Service and Productivity", © 2003 Neurostar Solutions. [online]. [retrieved Apr. 26, 2005]. Retrieved from the Internet: <URL: www.neurostarsolutions.com/index/jsp?page=PressRelease&newsID=2>, (2003), 3 pgs.

"Comply Product Overview", Strategic Management Group LLC. [online]. [retrieved on Nov. 2, 2006]. Retrieved from the Internet: <URL: http://www.complysoftware.com/>, (2006), 2 pgs.

"Credentialing Software from Intellisoft", Intellisoft Group, Inc. [online]. [retrieved on Nov. 2, 2006]. Retrieved from the Internet: <URL: http://www.intellisoftgroup.com/>, 3 pgs.

"Database Management System", © 2004 Fujifilm UK. [online]. [retrieved on Nov. 28, 2005]. Retrieved from the Internet: <URL: www.fujifilm.co.uk/synapse/technical/database>, (2004), 1 pg.

"Desktop User Interface", © 2004 Fujifilm UK. [online], [retrieved on Nov. 28, 2005]. Retrieved from the Internet: <URL: www.fujifilm.co.uk/synapse/product/desktop>, (2004), 2 pgs.

"Developing the Complete Teleradiology Infrastructure", The Hawk-The NightHawk Radiology Services Newsletter, (2005), 2 pgs.

"Diagna Radiology", [online]. [retrieved on Feb. 25, 2005]. Retrieved from the Internet: <URL: http://www.diagna.com/>, (2005), 12 pgs.

"Diagnosticimaging.com—Radiology is Going Places Let Us Take You There First", CMP Healthcare Media Group LLC. [online]. [retrieved on Nov. 30, 2005]. Retrieved from the Internet: <URL: www.diagnosticimaging.com >, (2005), 4 pgs.

"DICOM Conformance Statement for Cedara I-SoftView", Cedara Software Corp, Document No. 2004-02987, (2005), 1-38.

"EchoApps", Healthline Systems Inc. [online]. [retrieved on Sep. 6, 2005]. Retrieved from the Internet: <URL: http://www.healthlinesystems.com/echoapps_mc.asp>, (2005), 3 pgs.

"EchoApps—Simplify the Provider Application Process", © 2004 HealthLine Systems Inc. [online]. retrieved on Nov. 28, 2005]. Retrieved from the Internet: <URL: http://echomc.comlechoappsprocess2.asp>, (2004), 2 pgs.

"EchoApps Quick Tour, 12 Screen Captures", HealthLine Systems Inc. [online]. [retrieved on Nov. 28, 2005]. Retrieved from the Internet: <URL: http://healthlinesystems.com/demos/echoapps_demo.htm>, (2005), 13 pgs.

"EHR Clinical Overview", U.S. Department of Health and Human Services—Indian Health Service, [Online]. [retrieved on Jul. 15,

(56) References Cited

OTHER PUBLICATIONS

2005]. Retrieved from the Internet: <URL: http://www.ihs.gov/CIO/EHR/index.cfm?module=clinicaloverview>, (2005), 2 pgs.
"EMed—Test Drive Register", eMed® Technologies. [online]. [retrireved on Jul. 15, 2005]. Retrieved from the Internet: <URL: www.emed.com/products_services/matrix.php>, (2003), 4 pgs.
"Emergency Radiology Home Page", [online]. [retrieved on Nov. 12, 2006]. Retrieved from the Internet: <URL: http://www.emergencyradiology.net/missionstatement.htm>, (2006), 1 pg.
"Enterprise Image Management", GE Medical Systems, [online]. [retrieved on Jul. 15, 2005] Retrieved from the Internet: <URL: www.gehealthcare.com/img_info_systems/centricity_ris/products/enterprise_img.html>, (2005), 2 pgs.
"Epic Teleradiology Services", © 2006 Epic Teleradiology. [online]. [retrieved on Nov. 2, 2006]. Retrieved from the Internet: <URL: http://www.epictele.com/services.php>, (2006), 1 pg.
"European Application Serial No. 94908280.4, Entscheidung, vol. 9, Board of Appeal of the European Patent Office", (Feb. 2005). 19 pgs.
"European Application Serial No. 94908280.4, Office Action dated Feb. 8, 2005", (2005), 19 pgs.
"Ex Parte Re-examination Request re: Backhaus et al., U.S. Pat. No. 7,729,928 filed Dec. 17, 2010", (Dec. 17, 2010), 11 pgs.
"External Information System", © 2004 Fujifilm UK. [online]. [retrieved on Nov. 28, 2005]. Retrieved from the Internet: <URL: www.fujifilm.co.uk/synapse/technical/external>, (2004), 2 pgs.
"Fuji Receives Patent for Synapse's Subscription Technology", Fujifilm Medical Systems. [online]. [retrieved on Jul. 18, 2005]. Retrieved from the Internet: <URL: http://www.fujimed.com/company-info/press-room/doc/press_subscription_technology.asp?location=3&area=25&id=0&subid=0>, (2005). 2 pgs.
"Healthline Medical Imaging Modality Worklist DICOM Conformance Statement", Healthline Medical Imaging, (2005), 1-16.
"Healthline Medical Imaging Specification DICOM Conformance Statement", Healthline Medical Imaging, (2005), 27 pgs.
"HL7 Communications Module Definition Statement", Healthline Information Systems, Inc., (2005), 1-41.
"IDX® Imagecast tm Image Management—Radiology", [online]. (c) 1999-2005 IDX Systems Corporation. [retrieved on Jul. 15, 2005]. Retrieved from the Internet: <URL: www.idx.com/imagecast/ic_im_rad.asp>, (2005), 3 pgs.
"IHE Cardiology Technical Framework Supplement 2005—Displayable Reports (DRPT)", ACC/HIMSS/RSNA, (2005), 1-41.
"IHE Organization", IHE initiative: ACC/HIMSS/RSNA, [online]. [retrieved Nov. 30, 2005]. Retrieved from the Internet: <URL: http://www.ihe.net/About/Organization/org.cfm>, (2005), 3 pgs.
"Image Display Workstations", (c) 2004 Fujifilm UK. [online]. [retrieved on Nov. 28, 2005]. Retrieved from the Internet: <URL: www.fujifilm.co.uk/synapse/technical/display>, (2004), 2 pgs.
"Images Acquisitions System", (c) 2004 Fujifilm UK. [online], [retrieved on Nov. 28, 2005]. Retrieved from the Internet: <URL: www.fujifilm.co.uk/synapse/technical/image>, (2004), 2 pgs.
"Images to any Desktop with Synapse", Fujifilm Medical Systems, Synapse Intelligent Connectivity, (2003), 2 pgs.
"Imaging on Call Is a JCAHO Accredited Facility", © 2005 Imaging on Call LLC. [online]. [retrieved on Nov. 3, 2006]. Retrieved from the Internet: <URL: http://www.imagingoncall.net/company/jcaho.php>, (2005), 1 pg.
"Integrated Web Technology", (c) 2004 Fujifilm UK. [online]. [retrieved on Nov. 28, 2005] Retrieved from the Internet: <URL: : www.fujifilm.co.uk/synapse/product/webtechnology>, (2004), 2 pgs.
"International Application Serial No. PCT/US05/43212, International Search Report dated Sep. 26, 2007", 2 pgs.
"International Application Serial No. PCT/US05/43212, Written Opinion dated Sep. 26, 2007", 4 pgs.
"International Application Serial No. PCT/US2011/059926, International Preliminary Report on Patentability dated May 23, 2013", 12 pgs.
"International Application Serial No. PCT/US2011/059926, Search Report dated Mar. 1, 2012", 2 pgs.

"International Application Serial No. PCT/US2011/059926, Written Opinion dated Mar. 1, 2012", 10 pgs.
"Medical Licensure Services", [online]. [retrieved on Sep. 7, 2005]. Retrieved from the Internet: <URL: http://www.medlicense.comlservoces.htrnl>, (2005), 3 pgs.
"MedModel—The Industry Standard for Healthcare Simulations", [online]. [Retrieved on Sep. 7, 2005]. Retrieved from the Internet: <URL: http://www.promodel.com/products/medmodel>, (2005), 2 pgs.
"MedModel Simulation Plan your hospital and clinics using simulation software", Healthcare Planning Associates. [online], [retrieved on Nov. 29, 2005]. Retrieved from the Internet: <URL: http://www.hpa.co.nz/index.asp?fpar=13732555342>, (2005), 2 pgs.
"Misys PACS Integration Module (PIM)", Misys Hospital Systems, Inc. [online]. Retrieved from the Internet: <URL: http://www.misyshealthcare.com/NR/rdonlyres/11B3E4E4-B08B-4A78-970E-D37B8B69CCBF/0/misysPIMrev4.pdf#search=%22Misys%20PACS%20Integration%20Module%20(PIM)%22>, (2004), 2 pgs.
"Mobile Imaging", Empire Teleradiology Associates, LLC. [online]. [retrieved on Nov. 2, 2006]. Retrieved from the Internet: <URL: http://www.empiretelerad.com/emp_mobile,htm>, (2002), 1 pg.
"Multi-Site PACS with Synapse", © 2003 Fujifilm Medical Systems, Synapse Intelligent Connectivity, (2003), 2 pgs.
"National Practitioner Data Bank Healthcare Integrity and Protection Data Bank", NPDB-HIPDB, [online]. [retrieved Jul. 18, 2005], Retrieved from the Internet: <URL: http://www.npdb-hipdb.com/npdb.html>, (2005), 3 pgs.
"Network", (c) 2004 Fujifilm UK [online].]. [retrieved on Nov. 28, 2005]. Retrieved from the Internet: <URL: www.fujifilm.co.uk/synapse/technicaVnetwork>, (2004), 2 pgs.
"Night and Weekend Call Service", © RadLinx Group. [online]. [retrieved on Nov. 29, 2005]. Retrieved from the Internet: <URL: : http://www.radlinxgroup.com/nighthawk.html>, (2005), 3 pgs.
"Night Shift Radiology", Schematic of NightShift Radiology Network, NightShift Radiology. [online]. [retrieved on Nov. 28, 2005]. Retrieved from the Internet: <URL: http://www.nightshiftradiology.com/network.htm>, (2005), 2 pgs.
"Nighthawk Pros Premier Night-Time Coverage—Nighthawk Pros Company Profile, Teleradiology Overview of Services, Teleradiology Solutions for Radiology Experts, Teleradiology Technology Solutions", Nighthawk Pros. [online]. [retrived on Feb. 25, 2005], Retrieved from the Internet: <URL: http://www.nighthawkpros.com/>, (2005), 4 pgs.
"Nighthawk Radiology Services Contact Information—contact information, company information, services, network technology", Nighthawk Radiology Services. [online]. [retrieved on Feb. 25, 2005]. Retrieved from the Internet: <URL: http://www.nighthawkrad.net/>, (2005), 5 pgs.
"NightRays credentialing", NightRays. [online]. Retrieved from the Internet: <URL: http://www.nightrays.comIcredreq.pdf>, (publsihed before Mar. 7, 2007), 1 pg.
"NightShift Radiology—Overview", NightShift Radiology. [online], [retrieved on Feb. 25, 2005]. Retrieved from the Internet: <URL: http://www.nightshiftradiology.com/., (2005), 3 pgs.
"NightShift Radiology Preliminary Report, Sample Report", Nightshift Radiology. [online]. [retrieved on Feb. 25, 2005]. Retrieved from the Internet: <URL: http://www.nightshiftradiology.com/sample_report.htm>, (2001), 6 pgs.
"Nightshift Radiology: Our Network Built for Reliability", Nightshift Radiology. [online]. [retrieved on Nov. 28, 2005]. Retrieved from the Internet: <URL: http://www.nightshiftradiology.com/network.htm>, (2005), 2 pgs.
"Non-Emergency Solve the Demand for Radiologists", © 2006 Diagna Radiology, [Online]. [retrieved Nov. 3, 2006]. Retrieved from the Internet: <URL: www.diagna.com/nonemerg.htm>, (2006), 2 pgs.
"On Demand Access to data", © 2004 Fujifilm UK. [online]. [retrieved on Nov. 28, 2005]. Retrieved from the Internet: <URL: www.fujifilm.co.uk/synapse/product/ondemand>, (2004), 2 pgs.
"OneApp Credentialing Software", © 2005 SyMed Development, Inc. [online]. [retrieved on Sep. 7, 2005]. Retrieved from the Internet: <URL: http://www.symed.comlproducts/ oneapp>, (2005), 2 pgs.

(56) References Cited

OTHER PUBLICATIONS

"OneApp Product Tour", © 2005 SyMed. [online]. [retrieved on Nov. 28, 2005]. Retrieved from the Internet: <URL: http://www.symed.comlproducts/oneapptour-l.asp>, (2005), 6 pgs.

"Partners you can trust", International Teleradiology Corporation. [online]. [retrieved on Nov. 3, 2006]. Retrieved from the Internet: <URL: http://www.teleradiologyonline.com/index.htm >, (2006), 1 pg.

"Product Data AON Tool Set Software Release Version 3.0", Fujifilm Medical Systems, (2003), 2 pgs.

"Product Data Server Software Release Version 3.0", Fujifilm Medical Systems, Synapse Intelligent Connectivity, (2003), 2 pgs.

"Project Title: Developing a Prototype for a Nationwide Health Information Network Architecture", Request for Proposal (RFP) ONCHIT-3, Section C—Descriptions/Specifications/Work Statement, (2010), 9 pgs.

"Proscan® Reading Services™—World Leaders in Medical Imaging Interpretation", Proscan Reading Services. [online]. Retrieved from the Internet: <URL: http://www.proscan.comlfw/mainlfw_link.asp?URL=/_ filelib/FileCabinet/PDFIProScanReadingService.pdfOlo3FFileName%3DProScanReadingService.pdf&Titie=Reading%20Services%20Brochure>, (before Mar. 7, 2007), 9 pgs.

"Radiology PACS RadWorks 5.0 Standard", Wipro GE Healthcare. [online]. [retrieved on Jul. 15, 2005]. Retrieved from the Internet: <URL: www.gehealthcare.com/inen/it_solutions/rad_pacs/products/rad/msiisrwst2.html.html>, (2005), 3 pgs.

"Radiology PACS RadWorks 5.1 Standard", Wipro GE Healthcare. [online]. [retrieved on Jul. 15, 2005]. Retrieved from the Internet: <URL: www.gehealthcare.comlineniitsolutions/radpacs/products/radlradworks.html>, (2005), 2 pgs.

"Rapid Reliable Radiology Technology", StatRad. [online]. Retrieved from the Internet: <URL: http://statrad.com/technology.html>, (published before Mar. 7, 2007), 2 pgs.

"Rapid Response Radiology™", Consulting Radiologists, Ltd. [online]. [retrieved on Nov. 3, 2006]. Retrieved from the Internet: <URL: http://www.consultingradiologists.com/rapidresponse technology.htrn >, (2006), 1 pg.

"RIS Radiology Information System Online Data Entry for Nighttime Teleradiology Studies", Virtual Radiologic Consultants, Startup Guide v1.7,, (May 16, 2005), 19 pgs.

"RSI Difference", (published prior to Nov. 10, 2010), 3 pgs.

"Santa Barbara County Care Data Exchange", [online]. Retrieved from the Internet: <URL: http://www.chcf.org/documents/ihealthJSantaBarbaraFSWeb.pdf.>, (2007), 4 pgs.

"SkyRIS TeleRIS—Complete workftow, reporting and distribution solution for multi-contract radiology and teleradiology", ThinAir Data, (2004), 2 pgs.

"SkyRISE Enterprise—Enterprise speech recognition interfaced to existing HIS/RIS", ThinAir Data, (2004), 2 pgs.

"Software Solutions for Today's Healthcare Professionals", © 2006 Morrisey Associates. [online]. [retrieved on Nov. 3, 2006]. Retrieved from the Internet: <URL: http://www.morriseyonline.coml >, (2006), 1 pg.

"Special Report: What's all the noise about tele-radiology?", © The RadLinx Group. [online], [retrieved on Nov. 29, 2005]. Retrieved from the Internet: <URL: http://www.radlinxgroup.com/articie noise teleradiology.html>, (2005), 3 pgs.

"StatRAD—Rapid, Reliable Radiology", Welcome, About Us, Services, Jobs, Contact Stat Radiology, [online]. [retrieved on Feb. 25, 2005]. Retrieved from the Internet: <URL: http://statrad.com/index.html>, (2005), 9 pgs.

"Storage System", © 2004 Fujifilm UK. [online]. [retrieved on Nov. 28, 2005]. Retrieved from the Internet: <URL: www.fujifilm.co.ukJsynapse/technicaVstorage>, (2004), 2 pgs.

"Sy Med Simplifying Managed Care", © 2006 Sy.Med Development, Inc. [online]. [retrieved Nov. 3, 2006]. Retrieved from the Internet: <URL: http://www.symed.coml>, (2006), 1 pg.

"Synapse User's Manual Quick Reference Guide", Fujifilm Medical Systems, Software Version 3.0.0,2002, Fujifilm Medical Systems, (2002), 198 pgs.

"Synapse Version 3.0.0 Systems Administration Manual", Fujifilm, (2003), 1-55 pgs.

"Synapse ™ Version 3.0.0 Workstation Administration Manual", Fujifilm, (2004), 1-62.

"TDS Network Welcome", Teleradiology Diagnostic Service, [online]. [retrieved on Oct. 27, 2006]. Retrieved from the Internet: <URL: http://www.tdsnetwork.neti>, (2004), 2 pgs.

"Technical Features", © 2004 Fujifilm UK. [online]. [retrieved on Nov. 28, 2005]. Retrieved from the Internet: <URL: www.fujifilm.co.uk/synapse/technical>, (2004), 2 pgs.

"Technically, It's Important", © 2006 TeamHealth Radiology. [online]. Retrieved from the Internet: <URL: http://www.thteleradiology.comltechnology.htrn>, (2006), 3 pgs.

"Teleradiology Solutions about us, services, contact us", Teleradiology Solutions, [online]. [retrieved on Feb. 25, 2005]. Retrieved from the Internet: <URL: ttp://www.telradsol.com>, (2005), 4 pgs.

"Teleradiology: At Work Night and Day", Harris. [online]. [retrieved on Nov. 3, 2006]. Retrieved from the Internet: <URL: www.healthimaging.com/content/view/479/681>, (2006), 5 pgs.

"TeleShare", Dejarnette Research Systems. [online]. [retrieved on Sep. 7, 2005]. Retrieved from the Internet: <URL: http://www.dejarnette.com/1024/requestedpage.asp?Content=Products/>, (2004), 2 pgs.

"Templeton Radiology", Templeton Readings LLC. [online], [retrieved on Feb. 25, 2005]. Retrieved from the Internet: <URL: http://www.templetornadiology.com>, (2004), 9 pgs.

"Templeton Radiology Night Solutions", © 2004 Templeton Radiology. [online]. [retrieved on Nov. 29, 2005]. Retrieved from the Internet: <URL: http://www.templetomadiology.com/night_so1.htrn>, (2004), 2 pgs.

"Templeton Radiology Physician Credentialing", Templeton Radiology. [online]. [retrieved on Sep. 7, 2005]. Retrieved from the Internet: <URL: http://www.templetomadiology.com/pc.htrn>, (2005), 2 pgs.

"Templeton Radiology Radiology Services", Templeton Radiology. [online]. [retrieved on Nov. 29, 2005]. Retrieved from the Internet: <URL: http://www.idshealthcare.com/hospital_management/global/templeton_radiology/web_enabled dictation!. . . >, (2005), 3 pgs.

"Templeton Radiology RISIPACS website product information", (c) 2004 Templeton Radiology. [online]. [retrieved on Nov. 29, 2005]. Retrieved from the Internet: <URL: http://www.templetomadiology.com/pacs.htrn>, (2004), 2 pgs.

"Templeton Radiology RISIPACSIWEB/ARCHIVE managed solution", Templeton Radiology. [online]. [retrieved on Nov. 29, 2005]. Retrieved from the Internet: <URL: http://www.templetomadiology.com/pacs.htrn>, (2005), 6 pgs.

"Templeton Radiology Teleradiology Night Solutions", Templeton Radiology [online]. [retrieved on Nov. 29, 2005]. Retrieved from the Internet: <URL: http://www.idshealthcare.com/hospitat management/global/templetonradiology/templeton_mobile readings/.htrn>, (2005), 3 pgs.

"The Project", GlobalRad® Non-Profit Foundation. [online]. [retrieved on Nov. 3, 2006]. Retrieved from the Internet: <URL: http://www.globalrad.org/project.htrn>, (2006). 1 pg.

"The RadLinx Group Ltd.—FAQ's", [online]. [retrieved on Nov. 29, 2005]. Retrieved from the Internet: <URL: http://www.radlinxgroup.com/faq.html>, (2005), 2 pgs.

"The Work Flow Process", Imaging On Call, LLC. [online]. [retrieved on Nov. 3, 2006]. Retrieved from the Internet: <URL: http://www.imagingoncall.net/technology/sat.php>, (2006), 1 pg.

"ThinAir Data—Healthcare at the Speed of Thought", [online]. [archived on Nov. 11, 2004]. Retrieved from the Internet: <URL: http://web.archive.org/web/20041112045011/http://www.thinairdata.com>, (2004), 2 pgs.

"U.S. Based Client Services", © RadLinx Group. [online]. [retrieved on Nov. 29, 2005]. Retrieved from the Internet: <URL: http://www.radlinxgroup.comlc1ient.htrnl>, (2005), 2 pgs.

"US Radiology On-Call—Locations, Services, Technology, Radiologists, FAQ, Contact Us", [online]. [retrieved on Feb. 25, 2005]. Retrieved from the Internet: <URL: http://www.usroc.com/>, (2005), 7 pgs.

(56) References Cited

OTHER PUBLICATIONS

"US Radiology On-Call FAQ", US Radiology On-Call. [online]. [retrieved on Nov. 3, 2006]. Retrieved from the Internet: <URL: http://www.usroc.comlfaq.htrnl >, (2006), 2 pgs.
"US Radiology On-Call Radiologists", © US Radiology On-Call. [online]. [retrieved on Nov. 3, 2006]. Retrieved from the Internet: <URL: http://www.usroc.com/radiologists.htrnl >, (2006), 1 pg.
"US Radiology On-Call-Locations, Services, Technology, Radiologists, FAQ, Contact Us", US Radiology. [online]. [retrieved on Feb. 25, 2005]. Retrieved from the Internet: <URL: http://www.usroc.coml >, (2005), 7 pgs.
"Veritas Product data (V-FORM)", Veritas Medical Services, Inc. [online]. [retrieved on Sep. 7, 2005]. Retrieved from the Internet: <URL: http://www.veritasmed.comlproducts/>, (2005), 3 pgs.
"Virtual Radiologic™ Physician Services Operating Manual", Virtual Radiologic Consultants, Inc., (2005), 75 pgs.
"Vistar Technologies—Automated Credentialing Software CVOs and Medical Societies", (c) 2005 Vistar Technologies. [online]. [retrieved on Nov. 3, 2006]. Retrieved from the Internet: <URL: http://vistartech.comlcvomed.htrn >, (2005), 1 pg.
"Visual Cactus", Cactus Software. [online]. Retrieved from the Internet: <URL: http://www.visualcactus.com/Public2002/images/HospitalFlyer-2005.pdf.>,, (2005), 1 pg.
"VRN—A Step Beyond Teleradiology", © 2005 NeuroStar Solutions. [online]. [retrieved on Nov. 30, 2005]. Retrieved from the Internet: <URL: http://www.neurostarsolutions.com/cms/theVRN/vrnApplicationServices/pacs.html>, (2005), 2 pgs.
"Welcome to MedTel International", MedTel International. [online]. [retrieved on Nov. 3, 2006]. Retrieved from the Internet: <URL: http://www.medtel.coml >, (2006), 1 pg.
"Why the NPDB Was Created", National Practioner Data Bank. [online]. [retrieved on Nov. 30, 2005]. Retrieved from the Internet: <URL: http://www.npdb-hipdb.comlnpdb.htrnl>, (2005), 2 pgs.
"WIN/Staff PRO-FILE", WIN/Staff 002. [online]. [retrieved on Nov. 3, 2006]. Retrieved from the Internet: <URL: http://www.winstaff.comlmarketing/prac J>ro file.htrn >, (2002), 1 pg.
"World Wide Rad FAQ", World Wide Rad [online]. [retrieved on Nov. 3, 2006]. Retrieved from the Internet: <URL: http://www.worldwiderad.comlWWRWebsite files/frame.htrn >, (2006), 1 pg.
Batchelor, J. S, "Remote-controlled MRI tackles tech shortage", [online]. [retrieved on Jan. 26, 2006]. Retrieved from the Internet: <URL: http://www.auntrninnie.comlindex.asp?sec=ser&sub=def&pag=dis&ItemID=69371>, (2006), 2 pgs.
Brice, James, "Continued IT evolution boosts teleradiology", NightHawl Radiology Services, (Feb. 2004), 5 pgs.
Collins, J E, et al., "Automated Assignment and Scheduling of Service Personnel", IEEE Expert, (Apr. 1994), 33-39.
Finarelli, Hugo J, et al., "Effective demand forecasting in 9 steps Shifts in demand for a hospital's services can occur unexpectedly. Demand forecasting can help you prepare for these shifts and avoid strategic missteps", [online]. [retrieved on Feb. 22, 2012]. Retrieved from the Internet: http://findarticles.com/p/articles/mi_m3257/is_11_58/ai_n635908/, (Nov. 2004), 13 pgs.
Harrell, Charles R., et al., "Healthcare Simulation Modeling and Optimization using MedModel", *Proceedings of the 2000 Winter Simulation Conference, 2000*, Joines et al., eds., (2000), 203-207.
Khan, Rashid N, *Business Process Management: A Practical Guide*, (Sep. 2004), 103-124.
Khan, Rashid N, *Business Process Management: A Practical Guide*, (Sep. 2004), p. 179.
Khan, Rashid N, *Business Process Management: A Practical Guide*, (Sep. 2004), 207-222.
Khan, Rashid N., "Smart Ways of Routing Work, Business Process Management: A Practical Guide", [online]. Retrieved from the Internet: <URL: http://www.bpm.com/smart-ways-of-routing-work.html>, (Sep. 2004), 4 pgs.
May, T., "Home work may solve doe shortage", [online], [retrieved on Jan. 22, 2007]. Retrieved from the Internet: <URL: www.usrp.net/articles/Home work.htrnl>, (2007), 2 pgs.
Osborne, J. W., et al., "The Power of Outliers (and why researchers should ALWAYS check for them)", *Practical Assessment, Research & Evaluation*. 9(6), (Nov. 2004), 28 pgs.
Page, D., "To the ends of the Earth", Diagnostic Imaging, [online]. Retrieved from the Internet: <URL: www.diagnosticimaging.comlspecialedition20031?page=teleradiology.htrnl>, (2003), 7 pgs.
SkyRIS, "Full feature RIS with integrated speech recognition and transcription", ThinAir Data, (2004), 2 pgs.
Thinair Data, Skyris Teleradiology, "TeleRIS is the complete teleradiology, multi-contract, multi-facility workftow, reporting and distribution solution", [online]. [archived on Feb. 4, 2005]. Retrieved from the Internet: <URL: http://web.archive.org/web/20050204055213/www.thinairdata.com/SkyRISTele.htm, (2005), 3 pgs.
"U.S. Appl. No. 13/966,594, Final Office Action dated May 27, 2015", 11 pgs.
"U.S. Appl. No. 13/966,594, Non Final Office Action dated Dec. 5, 2014", 8 pgs.
"U.S. Appl. No. 13/966,594, Response filed Apr. 6, 2015 to Non Final Office Action dated Dec. 5, 2014", 12 pgs.
"U.S. Appl. No. 13/966,594, Supplemental Amendment and Response filed May 11, 2015 to Non-Final Office Action dated Dec. 5, 2014", 13 pgs.
"U.S. Appl. No. 14/079,307, Non Final Office Action dated Jan. 22, 2015", 12 pgs.
"U.S. Appl. No. 14/079,307, Response filed Jun. 22, 2015 to Non Final Office Action dated Jan. 22, 2015", 15 pgs.
"U.S. Appl. No. 90/009,889, Decision on Petition dated Aug. 1, 2012", 15 pgs.
"Canadian Application Serial No. 2,636,705, Office Action dated Mar. 26, 2015", 5 pgs.
"U.S. Appl. No. 14/079,307, Final Office Action dated Aug. 4, 2015", 16 pgs.
"Canadian Application Serial No. 2,636,705, Response filed Sep. 28, 2015 to Office Action dated Mar. 26, 2015", 11 pgs.
"U.S. Appl. No. 13/966,594, Non Final Office Action dated Dec. 24, 2015", 16 pgs.
"U.S. Appl. No. 13/966,594, Response filed Mar. 24, 2016 to Non Final Office Action dated Dec. 24, 2015", 19 pgs.
"U.S. Appl. No. 14/079,307, Non Final Office Action dated Feb. 8, 2016", 23 pgs.
"U.S. Appl. No. 14/079,307, Response filed Jan. 4, 2016 to Final Office Action dated Aug. 4, 2015", 25 pgs.
"U.S. Appl. No. 13/966,594, Appeal Brief filed Oct. 17, 2016", 37 pgs.
"U.S. Appl. No. 13/966,594, Appeal Decision dated Dec. 21, 2018", 22 pgs.
"U.S. Appl. No. 13/966,594, Final Office Action dated May 13, 2016", 12 pgs.
"U.S. Appl. No. 13/966,594, Response filed Sep. 28, 2015 to Final Office Action dated May 27, 2015", 19 pgs.
"U.S. Appl. No. 14/079,307, Appeal Brief filed Aug. 9, 2016", 24 pgs.
"U.S. Appl. No. 14/079,307, Appeal Decision dated Jun. 25, 2018", 23 pgs.
"U.S. Appl. No. 14/079,307, Examiner Interview Summary dated Jan. 31, 2019", 3 pgs.
"U.S. Appl. No. 14/079,307, Non Final Office Action dated Oct. 9, 2018", 20 pgs.
"U.S. Appl. No. 14/079,307, Response filed Feb. 8, 2019 to Non Final Office Action dated Oct. 9, 2018", 17 pgs.
"Canadian Application Serial No. 2,636,705, Final Office Action dated Apr. 4, 2016", 5 pgs.
"Canadian Application Serial No. 2,636,705, Office Action dated May 10, 2017", 2 pgs.
"Canadian Application Serial No. 2,636,705, Response Filed Jun. 28, 2017 to Office Action dated May 10, 17", 1 pg.
"Canadian Application Serial No. 2,636,705, Response filed Oct. 4, 2016 to Final Office Action dated Apr. 4, 2016", 6 pgs.
"U.S. Appl. No. 14/079,307, Notice of Allowance dated Mar. 28, 2019", 9 pgs.
"Canadian Application Serial No. 2,636,705, Summons to attend Oral Proceedings mailed Mar. 15, 2019", 8 pgs.

(56) References Cited

OTHER PUBLICATIONS

"U.S. Appl. No. 13/966,594, Non Final Office Action dated May 20, 2019", 16 pgs.
"U.S. Appl. No. 13/966,594, Examiner Interview Summary dated Jun. 3, 2019", 3 pgs.

* cited by examiner

MEDICAL IMAGE METADATA PROCESSING

CROSS REFERENCE TO RELATED CASES

This application is a continuation of and claims priority under 35 U.S.C. § 120 to U.S. patent application Ser. No. 13/423,513, filed on Mar. 19, 2012 entitled "Medical Image Metadata Processing," which is a continuation of and claims priority under 35 U.S.C. § 120 to U.S. patent application Ser. No. 12/856,096, filed on Aug. 13, 2010, entitled "Medical Image Metadata Processing," which is a continuation-in-part of prior U.S. patent application Ser. No. 12/783,073 filed May 19, 2010 and entitled "Multiple Resource Planning System", which is a continuation of prior U.S. patent application Ser. No. 11/288,645 filed Nov. 28, 2005 and entitled "Multiple Resource Planning System", which claims the benefit of U.S. Provisional Patent Application Nos. 60/656,215, filed Feb. 25, 2005 by Backhaus and entitled "Automated Credentialing and Licensing System"; 60/682,052, filed May 17, 2005, by Backhaus et al. and entitled "Integrated Caching Environment with Order Form Pre-population"; 60/694,880, filed Jun. 29, 2005, by Backhaus et al., and entitled "Medical Data Management Method and System"; 60/699,119, filed Jul. 14, 2005, by Backhaus et al., and entitled "Medical Data Transfer System and Method"; 60/740,454, filed Nov. 28, 2005 by Backhaus et al., and entitled "Medical Data Transfer System and Method"; 60/740,589, filed Nov. 28, 2005 by Casey and entitled "Remote Scanning System and Method"; and 60/740,527, filed Nov. 28, 2005 by Casey and entitled "Patient Information Translation Method and System"; the entirety of all of the preceding applications are incorporated herein by reference.

FIELD OF THE INVENTION

The present invention generally relates to medical image data processing and the evaluation of radiological images. The present invention more specifically relates to the extraction and use of metadata from radiological images and data transmissions, such as header metadata stored within images compliant with the DICOM (Digital Imaging and Communications in Medicine) standard.

BACKGROUND OF THE INVENTION

Medical images generated by an imaging modality, such as X-rays, CAT (Computerized Axial Tomography) scans, and MRI (Magnetic Resonance Imaging) scans, are commonly digitized to facilitate reading by doctors at remote locations. In use, hospitals and other healthcare providers commonly use systems to capture and digitize the medical images. The medical images are typically transmitted from the modality to a remote image server such as a Picture Archiving and Communications System (PACS). This transmission may occur over a network, such as an intranet or the Internet.

Additionally, the hospital may also transmit orders corresponding to the images to an order server, such as a Radiologist Information System (RIS). Orders are used to request a radiologist to interpret, or read, the images and return a diagnostic report. Orders may also contain additional information related to the image or the patient, such as a patient identifier, the procedure type associated with the image, patient demographic information, and a hospital identifier. Thus, orders may be submitted by hospitals and healthcare providers to identify the patient and instruct the radiologist to provide information for a specific medical condition.

Existing processing systems used in radiology practices generally route images and orders to radiologists in a fixed manner. For example, all of the images and orders may be transmitted from the scanning area of a hospital to a set of doctors that work in the radiology department of the same hospital. After receipt of the images and orders, the radiologist may analyze the image and return a diagnostic report. The diagnostic report may be transmitted through the network to the order server (the RIS), which in turn may forward the report to the hospital or other medical facility that originally transmitted the order and images corresponding to the report.

Although many types of PACS and RIS systems are used by healthcare providers, most PACS and RIS systems are not configured to communicate with each other and correlate orders with the actual images. Therefore, full integration of an order into a radiology workflow is not achieved. As an example, Synapse from FUJIFILM Medical Systems of Stamford, Conn. allows doctors to subscribe to a folder on a PACS. When new images arrive in that folder, a doctor receives notification that the images have arrived. The new images may be cached or stored on the doctor's remote system for viewing. However, the radiology order must be manually created, validated, and submitted before the doctor can proceed with his or her analysis of these images.

In connection with the generation and use of radiological images, information for the patient and the radiological procedure may be entered or separately stored in a variety of locations, potentially leading to redundant or inconsistent data. For example, the information may be provided at the imaging modality before the radiology technician conducts the imaging of the patient; the information may be provided within the radiological images (such as in the header of a DICOM-standard image); the information may be provided within the PACS storing the images; the information may be provided in a RIS as a radiology order is manually created; and the information may be provided from the hospital or healthcare provider's medical record system. Enhanced techniques are needed to improve the workflow speed and accuracy of orders and information involved with remote radiological readings.

BRIEF SUMMARY OF THE INVENTION

One aspect of the present invention relates processing radiology orders and images using medical image data, such as metadata stored directly within a digital radiology image file. In one specific embodiment, a series of radiology image data files are received at an image order processing server from a medical facility via a network connection. Each of the series of radiology image data files is generated by an imaging modality at the medical facility, or forwarded from a facility's PACS implementation, and contains metadata to accompany radiology image data.

At least one of the series of radiology image data files is processed using the image order processing server, resulting in the extraction of the metadata stored in the data files. In a further embodiment, metadata is retrieved from the first image data file received at the image order processing server. The data provided by one or more data fields within the extracted metadata is used to create and populate a radiology order. In still a further embodiment, metadata is provided by one or more data fields defined in the data transmission of the image data files, such as a data transmission of medical image data files compliant with the DICOM communication protocol.

The radiology order is electronically transmitted to the medical facility for verification, such as by a radiology technician or ordering physician. Responsive to verification (or changes followed by verification) of the radiology order, the radiology order is received from the medical facility at the image order processing server and processed further as required. Finally, the radiology order and the series of radiology image data files are transmitted from the image order processing server to a radiologist.

In some embodiments, the radiologist is selected from a plurality of radiologists by the image order processing server based on data fields within the metadata and information provided within the validated order. For example, data values such as patient identifier, a medical facility identifier, sex of the patient, age of the patient, a type of modality used to produce the series of medical images, a type of radiological procedure, an indication of whether the study is a preliminary or final read, a type of medical condition, and a type of scan for which the series of medical images relates to might be used to select the radiologist. Further, based on the medical facility identifier, a radiologist who is licensed and credentialed for performing reads for the medical facility might be selected from a pool of potential radiologists.

The radiology image data files may be stored in a DICOM format, in another industry-standard format, or in a proprietary format that is unique to the imaging modality or processing platform generating the medical images. The imaging modality may be a modality supported by the DICOM standard. In a further embodiment, the radiology image data files may be converted to another format or modified by the image order processing system prior to electronic transmission to the radiologist.

Another aspect of the present invention relates to processing radiology orders and images using medical image data, including cases where a radiology order is transmitted prior to transmission of the radiology image data. In one specific embodiment, radiology order data relating to a radiological examination of a patient is received from a medical facility at an image order processing server (such as a teleradiology processing server). The radiology image data is produced from the radiological examination and then received by the image order processing server.

The radiological image data is processed using the radiology processing server to extract metadata transmitted or stored with the image. Based on the image metadata, the radiology order is correlated to specific radiology image data. Further based on this metadata and medical specifications within the radiology order data, a radiologist may be selected from a plurality of radiologists. Selecting this radiologist may include selecting a radiologist based on data field values (such as a medical facility identifier). The radiology image data and the radiology order data may then be transferred to the selected radiologist consistent with the specifications of the radiology order.

Other embodiments of the present invention may provide for a system comprising a network and a radiology processing server configured for processing radiology orders and images, implementing the techniques described herein. Additionally, other embodiments of the present invention may provide for a computer program product for processing radiology orders and images, with the computer program product comprising a computer readable storage medium having computer readable program code embodied therewith to implement the techniques described herein.

DETAILED DESCRIPTION OF THE INVENTION

One aspect of the present invention relates to the use and processing of data obtained from medical images, and in one specific embodiment, the use and processing of medical and technical metadata that is provided within DICOM-format radiological image data files and data transmissions. In an illustrative embodiment, as medical images are received by an image processing system, metadata stored within the header of the DICOM-format medical image is extracted. This extracted data may be used to facilitate an improved operation of radiology processes, such as for use in the automatic creation and verification of a radiology read order. Further, this extracted data may be used to facilitate an enhanced workflow of the radiology study that may occur before or after the validation and submission of the order.

In a typical healthcare setting, an order must be validated and submitted before a radiologist can conduct his or her examination of a series of radiology images. The examination or "read" of this series of radiology images is generally referred to herein as a radiology study. The order to conduct the radiology study is typically entered and validated by the radiology technician or doctor at the location of the patient, e.g., at an imaging modality or at an emergency room. The order contains the necessary patient and medical information relating to the requested radiology study, such as providing instructions for the radiologist to identify a specific medical condition or to examine a certain area. After verification and submission, the order is then transmitted to a radiology department or directly to a radiologist along with the images for reading.

As is evident from the following description of an example radiology system configuration, the information that must be entered into the radiology read order may be duplicative of information already entered and stored in the medical image metadata or in other electronic medical record sources. In one embodiment of the present invention, the radiology read order may be created and pre-populated based on the metadata processed from one or more radiology images to be read in the radiology study.

Figure 1:
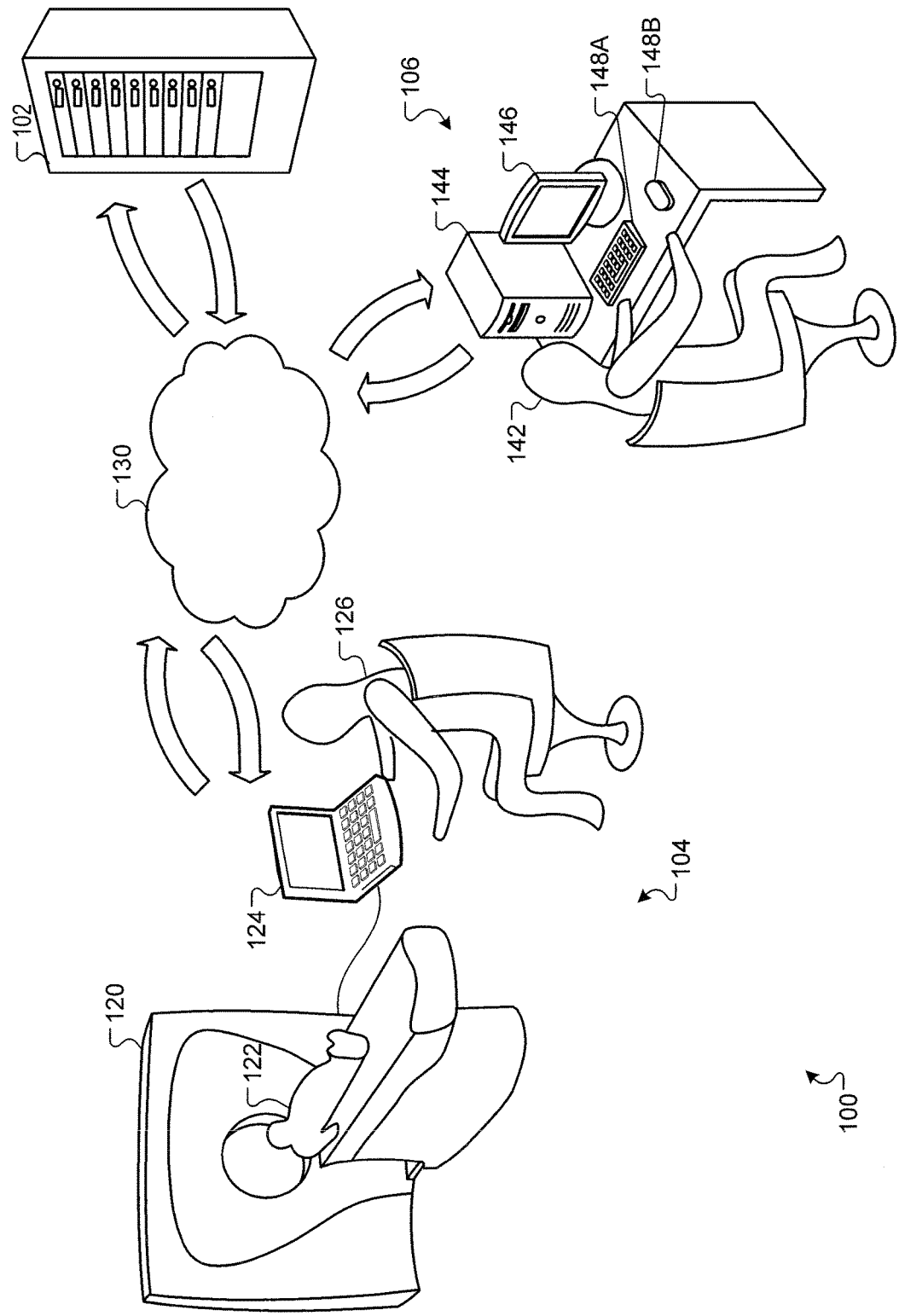
FIG. 1 provides an illustration of a radiology system used in conjunction with an embodiment of the present invention.

Referring to FIG. 1, a configuration of an example radiology system 100 is illustrated. The system 100 can be used for capturing medical image data in one location and for reviewing medical images associated with the data in another location. The system 100 may include many geographically separated imaging devices and many image review terminals. Therefore, system 100 might be configured to operate as a remote teleradiology system connected to a plurality of healthcare locations, or as a localized radiology system used in a single hospital, healthcare provider network, or private radiology practice.

For purposes of illustration, the radiology system 100 illustrated in FIG. 1 includes an imaging system 104, an image order (IO) management system 102, and an image review system 106. The imaging system 104, for example, may include an imaging device 120, such as a CT (computed tomography) scanner, an MRI (magnetic resonance imaging) scanner, ultrasound machine, or another imaging modality. Using an energy source such as x-rays or magnetic fields, for example, the imaging device 120 may capture image data associated with a subject 122 (e.g., a patient).

The imaging device 120 may be controlled by a radiology technician 126 through the use of a workstation terminal or other electronic control 124. Prior to the radiology technician 126 conducting the scan of a patient, information is entered into the terminal 124. In most medical devices, this information must be manually entered via an input device (such as a keyboard) operably coupled to the terminal 124. This information is then embedded with the image itself. For example, the imaging device 120 may produce radiological image data files generally consistent with the DICOM format, other industry-accepted standards, or in a proprietary format.

Consistent with the appropriate image format, the images produced by the image data source may include metadata. This image metadata may be generated by the imaging device 120 and/or by the technician input collected by the terminal 124. Further, the series of images may be obtained directly by the imaging device 120 in the facility shown in FIG. 1, or may be transferred in whole or in part from another image capturing device connected to the imaging device modality 120 or the facility's local network. The imaging data source may also be transmitted through use of a local facility imaging server (not shown), such as a DICOM server or other PACS.

As used in throughout present disclosure, metadata provided by the medical facility or imaging device 120 may refer to specific data fields and values provided in the imaging data itself (such as data fields in the header of each DICOM images), or specific data fields and values provided outside of the data image (such as metadata transmitted within a data communication compliant with the DICOM protocol). Those skilled in the art would recognize that numerous types and formats of metadata used in connection with medical image generation and transmission may be employed in radiology system 100, and are therefore within the scope of the present invention.

As a further example of metadata data values, the metadata within each imaging data file may include identification information such as patient identifier and an identifier of the series of images, in addition to information about the type of modality and the techniques used to obtain the images. Further, for images formatted according to the DICOM standard, data fields such as a unique image identifier, a unique study identifier, the patient's name, and the facility from which the image originates may be included.

The image data generated by the imaging device 120 may include a series of two-dimensional images. In some implementations, the image data may be used to produce a three-dimensional model that can be further manipulated and reformatted for generating two-dimensional (or three-dimensional) images. Image data captured by the imaging device 120 may be stored and processed by the IO Management System 102 or another imaging device server (e.g., one or more computers with a processor and a memory), and may be provided to other systems and computers in the system 100 through network 130 (e.g., an intranet or the Internet).

In some implementations, image data provided to the IO Management System 102 results in data being stored and processed by one or more computers. For example, the IO Management System 102 may determine that the image data is to be forwarded to a system user 142 (e.g., a radiologist) at an image review system 106. As shown, image data may be provided by the IO Management System 102 to the image review system 106 through the network 130.

The image review system 106, for example, may include an image display server 144 (e.g., one or more computers with a processor and a memory), one or more display devices 146 (e.g., monitors), and input devices 148A-B (e.g., keyboards, computer mice, joysticks, touch interfaces, voice recognition interfaces, and the like). In some implementations, image data may be processed by the image display server 144 and visually presented to the user 142 as one or more images at the display device 146. Using the input devices 148A-B, the user 142 may interact with the presented images, for example, by manipulating one or more user controls included in a graphical user interface presented at the display device 146 in association with the images. For example, the user 142 may view an image (or a series of related images), and may specify one or more image adjustments, such as zooming, panning, rotating, changing contrast, changing color, changing view angle, changing view depth, changing rendering or reconstruction technique, and the like. By viewing and interacting with presented image data and with the user interface, for example, the user 142 may produce and indicate a diagnostic finding related to the subject 122.

As further discussed below, when the IO Management System 102 receives the image, it may process the image with an image server component. This processing may include compressing or converting the image to a different format using a compressor/converter module. This image server component may also operate to extract metadata from each image file in a series of radiology scan images. For example, the extracted metadata may include header data for the image providing patient information and hospital information for the hospital that sent the image. The image server may then store all or part of the extracted information in a study record that may be correlated with appropriate orders and studies, or patient electronic medical records.

As previously suggested, within traditional radiology practices, a separate radiology read order with patient data is created independently of the patient data entered into the terminal 124. This leads to a set of data associated with the creation of the order into a RIS, and a set of data derived from the images that is ultimately compiled within a PACS. Therefore, when the radiology technician or doctor creates the radiology read order, the read order will be created with the same information already provided into the terminal 124 (or that is soon to be provided into the terminal), such as patient name. This duplicative information leads to unnecessary delay and the potential for errors.

In one embodiment of the present invention, metadata extracted from the images is used to pre-populate a radiology read order for verification by the radiology technician or doctor. This pre-population reduces the amount of manual data entry, and improves the accuracy and speed of the radiology order. Further, as suggested herein, the metadata from the images may be extracted in connection with an enhanced workflow, processing, and assignment of the radiology images and order.

Figure 2:
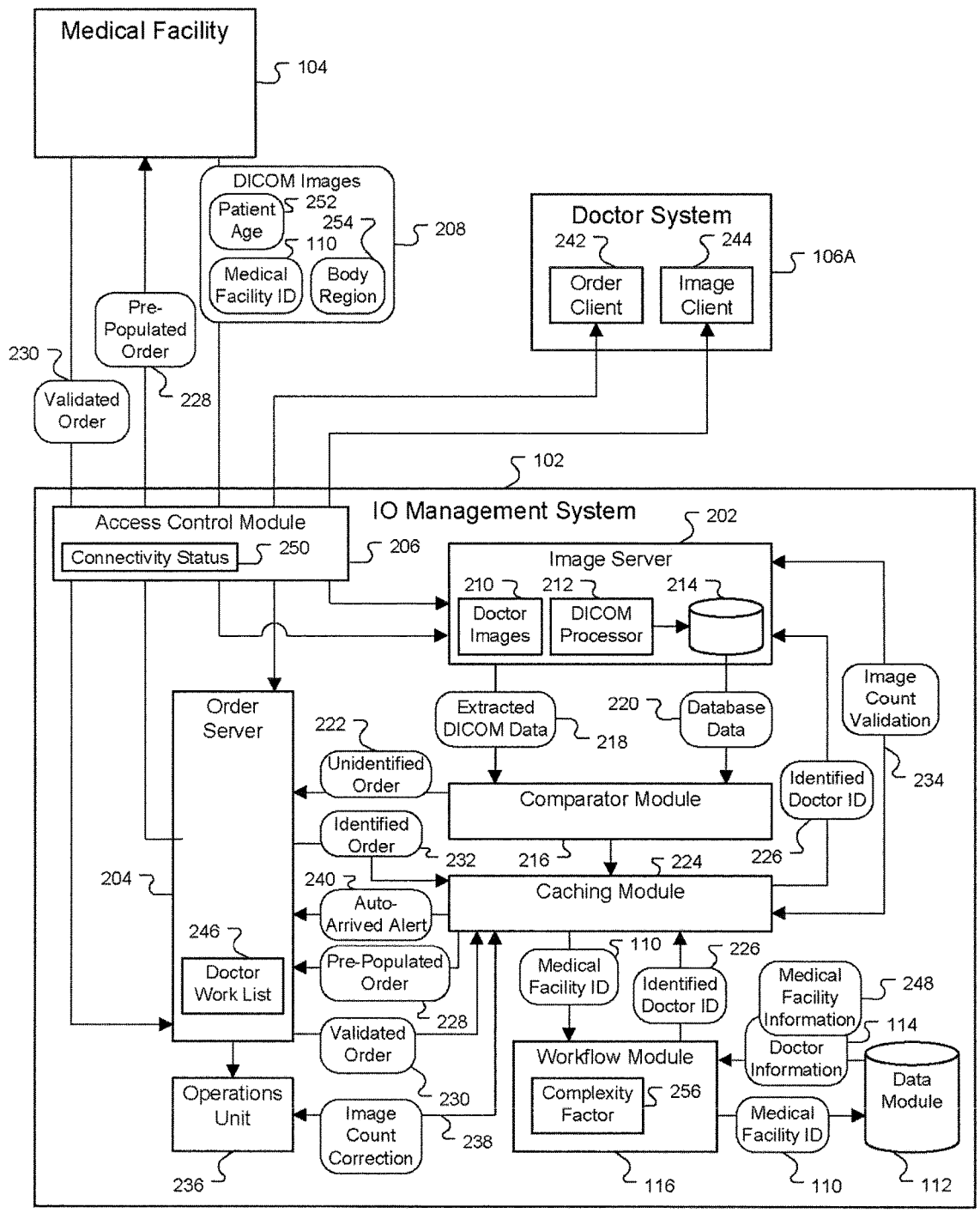
FIG. 2 provides a block diagram of an image order (IO) management system for receiving and processing orders and images used in conjunction with an embodiment of the present invention.

FIG. 2 provides a further illustration of the components within an example IO Management System 102 and interaction between the IO Management System and image data received from radiology devices of a medical facility 104 according to one embodiment of the present invention. This IO Management System 102 may contain or be interfaced with various components of a RIS and a PACS. These and other systems within the IO Management System may be physically located or operated at disparate locations, at a single processing center, or in whole or in part by a third party service provider.

Within the IO Management System 102, an image server 202 and an order server 204 receive images and orders, respectively, from the medical facility 104. The image server 202 and the order server 204 send the images and the orders to the doctor system 106A for review by a radiologist. An access control module 206 provides secure access to the IO Management System 102 from the medical facility 104 and the doctor system 106A.

As shown in FIG. 2, the medical facility 104 may send a medical request (e.g., a request for a radiologist review of electronic medical images) comprising DICOM images 208 to the IO Management System 102. The image server 202 receives the DICOM images 208. The image server 202 may be part of a PACS, which digitally stores, transmits, and displays medical images. The image server 202 may store the image files as images 210. A DICOM processor 212 extracts DICOM data from the images and stores the DICOM data associated with the images in a database 214. The images are assigned an identifier that is stored in the database 214 and is used to access the images when needed for transmission or other purposes. When received, a compressor (not shown) may compress the images using a variety of compression algorithms to compress the images, such as JPEG, JPEGLS, JPEG2000, PNG, GIF, XBM, BMP, and TIFF.

The compressor may be implemented on the same computing device as the image server 202. In one implementation, the image compressor may be accessible by the software that executes the functions of the image server 202. For example, the image compressor may be a dynamic load library (DLL) code segment stored on the same computing device and accessed by the image server 202. Alternatively, the compressor may be implemented on a separate computing device from the image server 202. For example, the compressor may be accessible to software that executes the functionality of an Internet server, which is resident on a separate machine from the image server 202. The Internet server may access the compressor whenever it receives images from the image server 202 for transmission to the network.

Additionally, the database 214 and the images 210 may be stored at the image server 202. For example, the images and database may be stored on same machine that executes the image server software. This may simplify the operation and maintenance of the software. Alternatively, the images and database may be stored on a different machine from the image server. For example, the database may be installed on its own machine that has increased security protections and is isolated from the network in order to protect the medical data stored in the database. Similarly, the images may be installed on a separate machine that provides more storage capacity and specialized hardware that facilitates quick and efficient retrieval and storage of the images. After the workflow module assigns the orders and corresponding images to the selected doctors, the image server 202 may transmit the compressed images over the network to the doctor system 106A.

In one embodiment configured to process DICOM-formatted images, a comparator module 216 receives extracted DICOM data 218 and database data 220 from the image server 202. The image server extracts the original DICOM data from the images 210 again and transmits it to the comparator module 216 for comparison with the database data 220. The comparison may be used to determine if the DICOM processor 212 stored the extracted data correctly and under the correct patient name. For example, if the medical facility ID 110 provided by the medical facility 104 is not unique within the database 214 the workflow module 116 may be unable to provide the correct ID to the data module 112 to filter the medical request. In addition, if a patient name included in the database data 220 and associated with the medical request does not match a patient name specified in the DICOM data 218, then the request may be incorrectly associated with the patient. If the request is incorrectly associated, then the comparator module 216 sends an unidentified order 222 to the order server 204 for correction. Otherwise, the comparator module 216 provides the medical facility ID 110 derived from the DICOM data included in the medical request to a caching module 224.

The caching module 224 caches information related to the medical request. The caching module 224 transmits the medical facility ID 110 to the workflow module 116. The workflow module transmits the medical facility ID 110 to the data module, which may use the facility ID 110 to access doctor information for doctors credentialed at a medical facility specified by the facility ID. The data module 112 then returns the doctor information to the workflow module 116. Additionally, the data module may return medical facility information 248, such as how many requests per day the facility is contracted to request. The workflow module then performs filtering algorithms to determine a doctor to receive the request and returns an associated doctor ID 226 to the caching module.

The caching module 224 sends the identified doctor ID 226 to the image server 202. The image server 202 may place the images included in the medical request in file folders, or directories, which are associated with the identified doctor ID 226. Alternately, the images may be transmitted directly to a remote location or server. The caching module 224 generates a pre-populated order 228 using the extracted DICOM data 218 and sends the pre-populated order 228 to the order server 204. In one specific embodiment, the pre-populated order serves as a formal order to read radiology images and is pre-populated with patient and hospital information, such as the hospital and patient name.

The order server 204 sends the pre-populated order 228 to the medical facility 104. The medical facility 104 validates the information contained in the pre-populated order 228 and sends the validated order 230 to the order server 204. For example, staff at the medical facility 104 may check the pre-populated information for correctness and specify or validate a number of images included in the request, a reason for the request, and a medical history of the patient. After receipt of the validated order, the order server 204 sends the validated order 230 to the caching module 224.

Unidentified orders 222 may also be corrected and then transmitted to the caching module 224. For example, personnel at the medical facility 104 may contact an operator with access to the order server. The medical facility personnel may provide the correct patient identification and other necessary information to correct the unidentified order 222. The operator may then correct the order 222, allowing the corrected order to be transmitted to the caching module 224 as an identified order 232.

In another implementation, unidentified orders 222 are corrected by transmitting a pre-populated order 228 to a "best guess" or "most likely" medical facility for confirmation. For example, the DICOM image header information associated with the unidentified order 222 may be used to generate a pre-populated order that includes the patient's name and other extracted information. If the originating facility is uncertain, the order server 204 may determine the medical facility with the highest probability of being the originating facility. The order server may then transmit the pre-populated form with the patient information for confirmation. If the order server determines that more than one medical facility matches information from the DICOM header, the order server may send a pre-populated form to all the matching medical facilities. The confirmed order is ultimately then transmitted to the caching module 224.

In one implementation, in addition to image metadata received within the medical imaging files, other metadata values may be provided by data communications between a medical facility and the IO Management System 102. For example, a facility identifier may be provided within metadata from a data transmission compliant with the DICOM communication protocol. This communication may be configured to contain metadata that embeds a facility ID or other usable data. In this way, identification of the sending facility may be achieved independent of any imaging metadata. As is apparent, numerous other data fields and values relevant to processing at the IO Management System may be provided within the data transmission metadata.

As images included in a medical request are received, the caching module 224 queries the image server 202 to determine if the correct number of images have been received, as indicated by arrow 234. If there are either too few or too many images received, then the caching module 224 refers the medical request to an operations unit 236 where the image count is corrected, as indicated by arrow 238. In one implementation, the image count is manually corrected by an operator that may contact personnel at the medical facility to inquire about the image count. When the image count is correct, the caching module 224 sends to the order server 204 an auto-arrived alert 240, and the order associated with the received medical images is placed in the doctor work list 246 associated with the doctor assigned to review the medical request.

The order server 204 sends the validated order 230, which is in the doctor's work list 246, to the order client 242 at the doctor system 106A. The image server 202 transmits the images to an image client 244 at the doctor system 106A. The doctor system 106A is associated with the identified doctor ID 226 and it is accessible by the identified doctor. The doctor may then review the images 208 and the order 230 associated with the request. Ultimately, the doctor generates a report based on the review and the report is sent to the medical facility 104, either directly or through the IO Management System 102.

As suggested above, the IO Management System 102 may be operably coupled to or otherwise directly contain the processing functionality of a RIS for use in a teleradiology setting. Specifically, in a teleradiology setting, the use and extraction of header data from images allows a request for a radiology read to follow a predefined workflow, in addition to having a radiology order be pre-populated and/or automatically created based on the images transmitted to the teleradiology provider.

In a teleradiology embodiment, a RIS interface may be provided to allow hospitals and medical facilities to enter and verify patient orders and all associated data electronically with the teleradiology provider. The teleradiology RIS may use information originating from the headers of the sent images and processed within the IO Management System to create and pre-populate data. Pre-populating data within the RIS interface may assist the technician in reducing the amount of data entry, while the RIS may also ensure that the data supporting the study is complete and consistent. For example, some of the RIS interface fields such as patient name and identifier may be automatically populated or updated from the DICOM header of the first image received by the teleradiology provider; although this information is only as accurate as the information in the DICOM header of the image.

Using the RIS interface in a teleradiology embodiment allows the hospital or medical facility to quickly validate and submit a radiology read order for a particular study. The hospital or medical facility may be able to access the pre-populated radiology read order within the RIS interface as soon as the first image is received and processed by the teleradiology provider—even if all of the images for the study have not yet been received or processed. Also, upon verification, data entry, and submittal of the radiology read order, the read order may be transmitted or become immediately visible to the radiologists credentialed for the specific facility or otherwise assigned to read the radiology study. This provides a significant improvement over other order request methods such as fax, which do not allow such wide and rapid distribution of order information. Further, processing these steps with the first image (or one of the first in the series of images) received greatly decreases the span of time to review and validate the order, and thus greatly decreases the amount of time before the radiologist can proceed with the study reads.

The teleradiology RIS may be configured to allow the medical facility staff to directly monitor the status of an order. For example, technicians and other users may confirm that an order has been submitted and that all appropriate studies have been requested. The RIS may also allow submitted orders to be modified or updated, prior to reading. A complete worklist may be viewed, showing all orders and their status, and whether orders are awaiting reading, currently undergoing reading, or have been read and results distributed.

The radiology read order may contain information about a patient, such as name, medical history, and the reason for creating the image. The order may also include a description of an associated image, such as a pelvic abdominal scan, a number of images associated with the order, and an order type, such as preliminary or final read. The presence of the patient name and other patient information may enable a particular image to be linked with a particular order in the RIS.

In one embodiment, the teleradiology RIS obtains the following fields from the information listed in the image metadata (e.g., the DICOM headers) of the radiology image data files: a) Patient Name; b) Medical Record Number (MRN); c) Accession Number (when applicable); and d) Exam Time. Other data fields and values from the image metadata may be processed. For example, relevant values may be provided from the groups of metadata defined according to the DICOM standard, including sender information, patient information, scan information, and study information. The technician will then verify that all of this processed information is correct within the pre-populated radiology read order. Errors in the information from a DICOM header may result from incorrect configurations on a modality.

The teleradiology RIS may also use other fields that may be extracted from the DICOM headers of the radiology images, such as the Referring Physician and Patient Sex. Again, this information must be validated in the order by a technician or doctor before the order's submission to a radiologist. The teleradiology RIS interface may allow other fields to be filled out and provided manually or in an order interface. These include a date of birth and/or age, an examination date, and the time-sensitivity of the order (for example, a notation if the images originate from an emergency room order or are otherwise time-sensitive).

In one embodiment, the technician or doctor may use a web page, remote desktop, virtual private network (VPN), or other type of remote access to review the order within an interface of the teleradiology RIS. As an example of the type of information that may need verification includes the a) examination time and date; b) the number of images; c) the type of study or image-generating modality; d) indications from the scan such as contrast or non-contrast; and e) other information related to the type or orientation of the scan.

In one embodiment, verification of the pre-populated radiology order may be processed through use of a hospital client system configured to receive and display a radiology order form from the IO Management System 102. After the hospital order client receives the pre-populated order template, a technician may access the order, verify the pre-populated information, and enter any additional information that is needed to complete the order. For instance, the technician may verify that the patient name correlates to the medical record number listed in the pre-populated order. The technician may also enter additional information in the order, if it is not already present, such as data or an age for the patient, exam date, and the type of study which needs to be examined by the radiologist. The technician may then submit the order to the IO Management System as described above.

The technician may then submit the order to a radiologist for reading the patient's images. The technician may validate the order into the computing device and submit the order to the IO Management System 102. Validated orders associated with the images may be transmitted from the hospital to the IO Management System and ultimately forwarded to the appropriate radiologists.

The orders sent from the hospital or medical facility may be processed with the IO Management System 102 through use of an order server 204. The order server assigns the orders to the appropriate radiologists, and transmits the orders over the network, such as the Internet, to the assigned radiologists' systems. Each radiologist system may contain a computing device with components necessary to display the images, view the read orders, and return a report based on examination of the images. For example, radiologist system A may include a computing device with a display and an image decompressor. The images transmitted by the IO Management System are received from the network, decompressed by the image decompressor, and displayed on the display. The image decompressor may be implemented on the computing device, or on a separate computing device, and use decompression algorithms, such as the decompression algorithms associated with JPEG, JPEGLS, and JPEG2000. The images may be cached at the radiologist system. For example, the images may be saved to a local storage device in the radiologist system. In one implementation, only the image or images which are associated with a particular order assigned to and accepted by the radiologist at radiologist system A may be shown on the display. In another implementation, the radiologist may view images of former orders accepted by the radiologist or orders that the radiologist plans to accept. In other implementations, the radiologist may view images regardless of whether the order is or will be accepted.

In a further embodiment, information that is derived from or otherwise processed in connection with the image metadata may be used in connection with a workflow used for assignment and review of the radiology images. For example, in a teleradiology practice, order creation and processing may also involve selecting a remote radiologist from a plurality of radiologists to assign the radiology read request and the associated study images. Further, the workflow may be customized to send the radiology read request to a certain radiologist based on facility information (such as which radiologist is licensed and credentialed with the hospital or medical facility that is requesting the read) and patient information (such as selection of a pediatric radiologist based on the age within the patient information) indicated within the image metadata.

Figure 3:
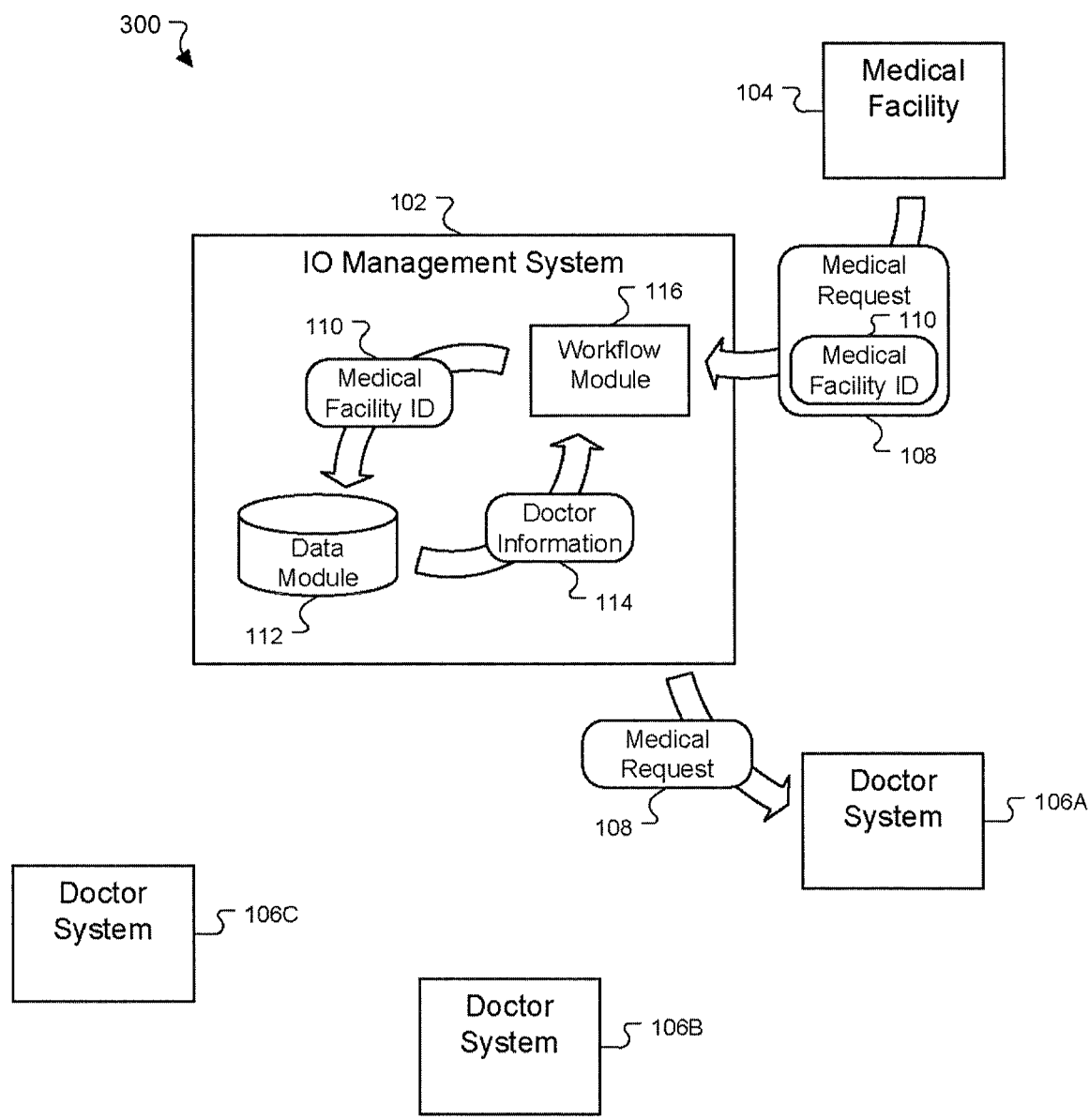
FIG. 3 provides a block diagram of a system for assigning medical requests to doctor systems used in conjunction with an embodiment of the present invention.

FIG. 3 further illustrates a system 300 for assigning medical requests (such as radiology studies) to doctor systems used in connection with such an embodiment of the present invention. As a non-limiting example, system 300 may be used by a teleradiology provider to collect and assign radiological images for reading by a plurality of radiologists at remote locations. System 300 may be adapted for use in a localized or semi-localized radiology practice to direct the workflow of a plurality of radiological image studies to a defined set of radiologists.

As shown in FIG. 3, medical facilities transmit the medical requests to an IO Management System 102, which implements a workflow module 116 that assigns the medical requests to selected doctors. The assignment may be based on several variables, such as whether the doctor is credentialed at the hospital, the doctor's schedule, the preference of the hospital for certain doctors, doctors' licensing status, compensation metrics, online status, geography, performance, and the volume and/or complexity of previous medical requests that have been assigned to a doctor. After assignment, the IO Management System 102 transmits the requests to the assigned doctor. In a further embodiment, a speculative assignment of an eligible radiologist(s) might be first performed based on preliminary information derived from the image and data transmission metadata, followed by the actual assignment or selection of the radiologist derived from verified information transmitted for the validated order.

To implement the medical request assignment, the system 300 coordinates the workflow between the IO management system 102, a medical facility 104, and doctor systems 106A-C. The IO Management System 102 performs operations to route medical requests from medical facilities, such as the medical facility 104, to one or more of the doctor systems 106A-C. The IO Management System 102 receives a medical request 108 (specifically, in this embodiment, a radiology study request), which includes a medical facility identifier (ID) 110, from the medical facility 104. The medical facility ID 110 is associated with the medical facility 104 from which the radiology study request 108 originated.

A data module 112 within the IO Management System 102 stores doctor information 114 including a doctor identifier, doctor schedule information, an order volume, a doctor classification composite metric, doctor location information, preference information, performance information, and contract terms (as suggested in FIG. 2). For example, a doctor may be identified within the data module 112 by a doctor ID. A doctor's schedule information may include times and dates that a doctor is scheduled to be available for reviewing medical requests. A doctor's order volume may indicate the number of medical requests that a doctor is capable of completing in a given period of time. A doctor's location may determine whether the doctor is allowed to review certain medical requests (e.g., doctors outside the United States may not be allowed to perform a final review of medical images). A medical facility's request for or refusal of a particular doctor may be indicated in the doctor preference information. A doctor's performance may be indicated by the accuracy of the doctor's reports or the satisfaction of medical facilities for which the doctor has reviewed medical requests. The contract terms of a doctor may specify a quota of medical requests the doctor is paid for regardless of the number of medical requests the doctor actually reviews. The contract terms may also specify a bonus rate for medical requests above the quota that are reviewed by the doctor.

A workflow module 116 receives the doctor information 114 and uses it along with the medical facility ID 110 to filter the radiology study request 108. In filtering the radiology study request 108, the workflow module 116 identifies one or more doctors to receive the request 108. The IO Management System 102 transmits the radiology study request 108 to each doctor system 106A, which is accessible by the doctor(s) identified during the filtering of the medical request. Consistent with the implementations described herein, the radiology study request 108 may include or reference an image, an order, or both.

To filter the radiology study request 108, the workflow module 116 transmits the medical facility ID 110 to the data module 112. The data module 112 uses the medical facility ID 110 to access and transmit the doctor information 114 associated with the medical facility ID. For example, the data module 112 may use the medical facility ID 110 as a key in a database table to locate all the doctors credentialed at a hospital specified by the medical facility ID 110. In this implementation, the data module 112 performs a first pass filter by providing to the workflow module 116 the doctor information 114, which contains a list of doctors credentialed at the medical facility 104.

In another implementation, the returned list of doctors may be a subset of all the doctors credentialed at the medical facility 104. For example, the data module 112 may only return a list of credentialed doctors that are scheduled to work (as indicated by the doctor scheduling information stored in the data module 112) when the medical facility ID 110 is received by the data module 112. In addition to selecting the appropriate doctor on the basis of the doctor's schedule, specialization, credentialing, and licensing, other external factors such as medical facility preferences and teleradiology provider preferences may be factored into this workflow and the ultimate assignment of the radiology study request to one or more doctors.

For example, the workflow may need to determine and consider licensing information related to whether a doctor is licensed in a particular state to practice medicine, and credentialing information related to whether a doctor is credentialed, or has privileges or is otherwise authorized, to perform medical services for a particular hospital. The query formulated by the data module may include the information directly or indirectly extracted from the image. Further, the workflow may factor based on the hospital information which doctors are licensed in the hospital's state and which doctors are credentialed at that hospital, which may have precedence over a specialization. Thus, if the information extracted from the image metadata indicates the type of procedure to which the image relates, such as a head scan, the workflow may also factor which doctors specialize in this type of image reading (while factoring that this scan cannot be given to a doctor who is not licensed or credentialed for this facility).

Based on a combination of the extracted and computed data, which may include the patient information, the image associated with the patient, the hospital information, and the individual doctors that are eligible to examine the images associated with the patient, the radiology study may be assigned to a particular radiologist. In one embodiment, the image server of the IO Management System transmits or places the images in folders, each folder being associated with an individual radiologist that is eligible to examine the images. The folders may be logical folders, such as directories on a server. The image server may also put additional information associated with the images in the eligible doctors' folders, such as any of the information contained in the study record or in the radiology read order. The image server may then transmit the images to the eligible doctor's radiologists systems. For example, if Dr. A is an eligible doctor, the images and the study record may be placed in Dr. A's folder, and then transmitted by the IO Management System to the Radiologist system A through a network, such as the Internet. The doctor using the Radiologist system A may then use an image client to view the images and/or the radiology read order.

Figure 4:
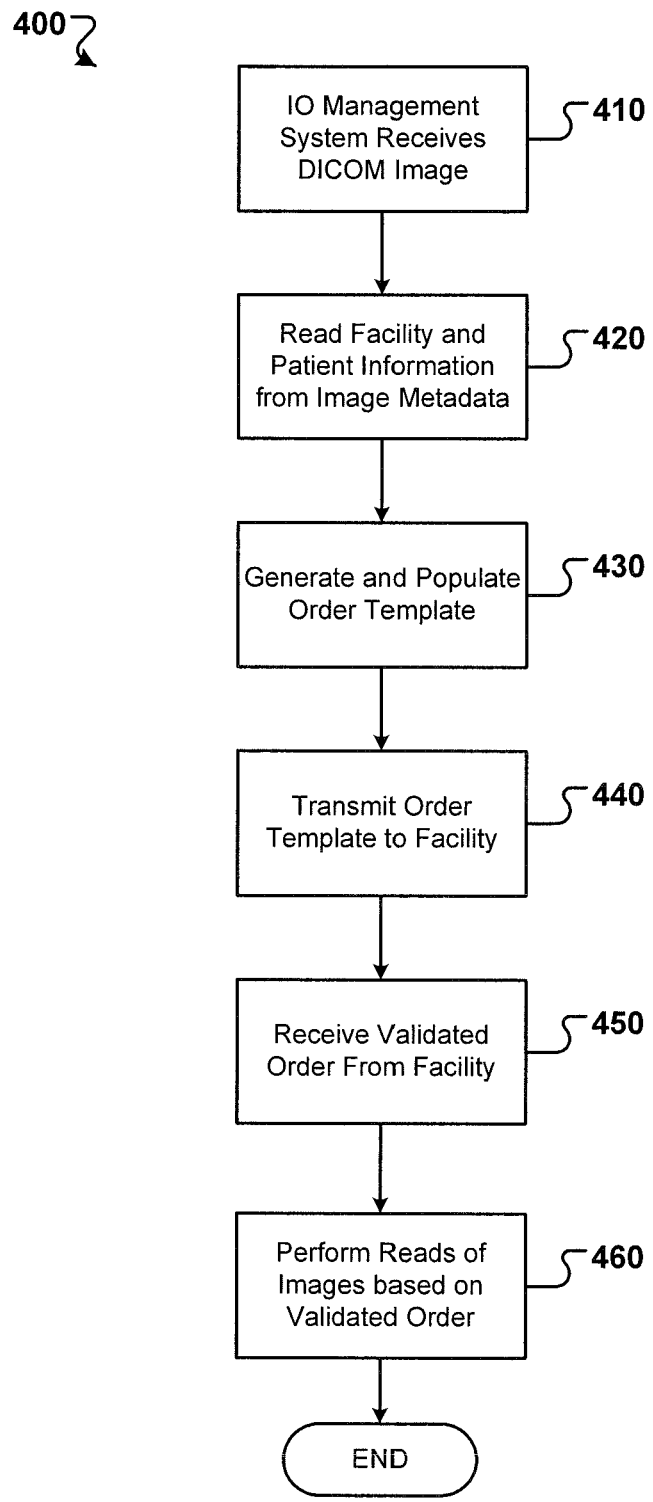
FIG. 4 provides a flowchart of an example operation for processing and creating an order from a medical image in conjunction with an embodiment of the present invention.

FIG. 4 provides a flowchart of a summarized method for pre-populating radiology read orders using information extracted from radiology images related to the read orders according to one embodiment of the present invention. Step 410 illustrates that the IO Management System receives an image. Consistent with the processing methods described above, a hospital or other medical facility may send one or more images to the IO Management System using the Internet or other network. Next, in Step 420, the medical facility and patient information is extracted from the image metadata through use of the IO Management System. For example, a DICOM image may contain a header with metadata that includes the patient's name and other related information, the transmitting facility's information including an identifier, and the image type.

In Step 430, an order template is generated and populated with information extracted from the image. For example, a radiology read order may be created and pre-populated with the patient's name and information from the facility that transmitted the images. This information in the image metadata will have originated from input by the radiologist technician or another medical professional input into the image modality or an image processing system within the medical facility. The pre-populated order may then be transmitted back to the medical facility that generated the image as in step 440.

Facility personnel may then receive and/or access the pre-populated order as in step 450 to verify the pre-populated information. This may be performed through use of an interface directly to the IO Management System, a teleradiology RIS, or the like. In this interface the facility may also enter additional information (such as critical medical details or physician instructions) related to the radiology study examination. Finally, the medical facility will submit the validated order and transmit it back to the IO Management System or teleradiology RIS, and a radiologist will conduct a read of the images based on the order as in step 460.

In other embodiments, the IO Management System or teleradiology RIS may receive the extracted information correctly from an image server or access a study record that contains the extracted image information. Additionally, the process steps depicted in FIG. 4 may operate concurrently or in slightly different order. For example, the information may be extracted from the image while the order module is generating the order template and the fields may be pre-populated as the extracted information becomes available.

A number of embodiments of the invention have been described. Nevertheless, it will be understood that various modifications may be made without departing from the spirit and scope of the invention. The images may contain data stored within Digital Information in Communications and Medicine (DICOM) formatted files, or data stored consistent with other industry-standard and proprietary formats. Likewise, the information and format of the metadata within the images may vary significantly, such as including the number of images in the transmission, the name of the patient, a name of the medical facility, and a name of a device within the medical facility where the image was created. Other information relevant to the patient's medical care such as insurance information may also be provided within the image metadata. In some implementations, the medical facility ID comprises the name of the medical facility and the name of the device.

In other embodiments, the medical request may comprise information or images in a format other than DICOM format. For example, the medical request may comprise images in CTI ECAT 7 image format, which originated from CTI Molecular Imaging, Inc. of Knoxville, Tenn. A processor may extract the ECAT 7 data from image headers and store the information in the database or other data store. The processor may recognize the ECAT 7 file type by parsing the header and determining if a text string "MATRIX71" is at location 0 of the file. After the file is identified, information about the patient, such as name, age, and gender, may be extracted from the file along with additional information, such as the facility identifier.

Additionally, the configurations and scenarios associated with a radiology workflow or need for radiology image processing may vary. Medical facilities may send images and orders at the same time as one another or at different times. For example, in some implementations, the medical facility sends the order before the images. In these implementations, the pre-populated order is not transmitted by the order server to the medical facility, but the order is completed in full by personnel at the medical facility.

Images, orders, and reports may be sent over the same network or different networks. For example, the IO Management System may receive images and orders through a single T1 or T3 connection to the Internet, or the images may be received from the Internet through a T1 or T3 connection and the orders may be received through a modem connection. In another example, the IO Management System may receive an image and an order from a medical facility over the Internet and return a corresponding report to the medical facility over a fax connection.

Additionally, the images and orders may be sent separately or combined in one transmission. For instance, a computing device at a medical facility may use software that sends the orders and the images with a single application and single set of actions, or the medical facility may send the images using one application that sends one transmission and send the orders using a different application that sends a separate transmission.

The network over which the images and orders are sent from the hospital or medical facility to the IO Management System may include a secure tunnel, such as a virtual private network (VPN). The VPN may include a secure computing device, or terminal, at the hospital, encrypted transmissions sent through the network, a secure computing device at the JO Management System, and a secure computing device at the radiologist systems. The transmission of encrypted images and orders may also include the use of other forms of secure communications, such as Secure Socket Layer (SSL), Terminal Services, and Citrix systems. Images and orders may be sent from multiple hospitals at the same time or at different times. For instance Hospital A, Hospital B, and Hospital N may submit images and orders simultaneously or serially over the Internet.

The IO Management System may be implemented on a single computing device or on multiple computing devices, such as a server farm or in a cloud-computing setting. In one implementation, the IO Management System may be disbursed over several servers that are connected through a network. This configuration may be advantageous by facilitating expansion of the system and flexibility in managing the flow of received and output images and orders.

The order module and the image module may be implemented on the same computing device or separate computing devices. For example, if the order module and image module are implemented on separate servers in the server farm, they may communicate with each other through a private network or a secure channel via the Internet. This architecture may permit the image module and order module to be placed at different physical locations, which may facilitate maintenance, upgrades, and repair.

The radiology read order that is received by the computing device at the radiologist system may or may not be accepted by the radiologist. If the order is accepted, the radiologist may view the images associated with the order, make a report based on the images, and transmit the report back to the IO Management System through the network. For example, the radiologist may dictate the report using speech recognition software installed on the computing device, and the computing device may send the generated report back to the IO Management System. The radiologist may also enter the report through a keyboard or other input device.

Additionally, the radiologist system may contain more than one computing device. For instance, there may be one computing device that accepts the images, decompresses them, and displays the images for the radiologist. The other computing device may handle receiving the orders, displaying them to the radiologist for acceptance, receiving the report from the radiologist, and transmitting the report to the IO Management System. The radiologist may also not accept the order. For instance, if the radiologist accessing the system is currently viewing an order previously received, the radiologist may not be able to accept another order until the previous order is completed. In this situation, a different radiologist may accept the order at another system. This is possible because the IO Management System may send the order to more than one radiologist system. Once a radiologist at one radiologist system accepts an order, the IO Management System may remove the order from the other radiologist systems.

The radiologist's report may be received at the IO Management System, where it may be formatted by the order module and sent to a fax system. The report may then be transmitted to a fax in the hospital that originated the order associated with the report. The fax system may contain several faxes to handle multiple reports simultaneously. Alternatively, the report may be sent to the hospital using the Internet. For example, the report may be sent in an e-mail to an SMTP (Simple Mail Transfer Protocol) server, where it is transmitted to the hospital via the Internet. Additionally, the report may be sent to a printer. After the report is printed out, it may be mailed or otherwise transmitted to the hospital. Alternatively, the report can be viewed via a web-based application via a standard internet browser or mobile device.

In further embodiments, a Hospital RIS can request and/or submit an order from the IO Management System using HL7 standard communications. For example, an order that is entered and submitted with a hospital information system may communicate with the teleradiology RIS using HL7 communications to obtain a pre-filled radiology read request. Given the high reliability of such data, this read request may then be automatically validated without manual review by a human technician. As soon as metadata from the images is processed by the IO Management System, the IO Management System may correlate these images to the previously validated order and forward the read order to the radiologist. In this way, the order may be automatically pre-populated, validated, and submitted by the medical facility provided that the images and HL7-initiated order data correlate to each other.

In further embodiments, facility preferences and settings may be factored in connection with the extraction of the metadata from the medical images. As discussed above, the selection of the radiologist from a pool of available radiologists may be derived from these facility preferences and settings. Additionally, other preferences such as the format of the eventual report and other processing changes may occur within the IO Management System or the radiologist's report as a result of the facility preferences and settings.

Information derived from the image metadata and extracted by the IO Management System may also be used in connection with billing, electronic medical records, and other health data uses that are not directly related to the workflow of the radiology image. Likewise, further embodiments of the present invention may correlate the data extracted from the image metadata to information from billing, electronic medical record, and other health data systems.

The features of the present invention described herein may be implemented in digital electronic circuitry, or in computer hardware, firmware, software, or in combinations thereof. For example, a computer program product designed to perform functions of the described implementations may be embodied in one or more computer readable medium(s) having computer readable program code embodied thereon; an apparatus such as a computing system with a processor and memory may embody components structured to perform functions of the described implementations; and method steps may be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A program is generally a set of instructions that can be used, directly or indirectly, in a computer or other electronic programmable device to perform a certain activity or bring about a certain result. A computer program can be written in any form of programming language, including compiled or interpreted languages, and it can be deployed in any form, including as a stand-alone program or as a DLL, module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include solid state drives; magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

Although various representative embodiments of this invention have been described above with a certain degree of particularity, those skilled in the art could make numerous alterations to the disclosed embodiments without departing from the spirit or scope of the inventive subject matter set forth in the specification and claims.

What is claimed is:

1. A data processing system, comprising:
   at least one hardware processor;
   an image processing component implemented by a first plurality of instructions executed with the at least one hardware processor, the image processing component to, under computerized control:
     extract data values from a set of electronic imaging data that includes a plurality of digital medical images, the plurality of digital medical images originating from a medical imaging procedure performed by a medical imaging modality at a medical facility;
   an order processing component implemented by a second plurality of instructions executed with the at least one hardware processor, the order processing component to, under computerized control:
     extract data values from electronic order data, wherein the electronic order data includes data provided to the data processing system that originates from the medical facility, and wherein the electronic order data specifies characteristics of a diagnostic evaluation task for the plurality of digital medical images;
associate the plurality of digital medical images in the data processing system with the electronic order data based on data values provided in the electronic imaging data;
a medical data processing component implemented by a third plurality of instructions executed with the at least one hardware processor, the medical data processing component to, under computerized control:
generate data values that identify characteristics of the diagnostic evaluation task for the plurality of digital medical images, based on the data values extracted from the electronic order data; and
perform an evaluation of parameterized qualification characteristic data values for a plurality of evaluators to perform the diagnostic evaluation task, using the identified characteristics of the diagnostic evaluation task, the evaluation to apply rules which identify respective evaluators that are credentialed or licensed to perform the diagnostic evaluation task for the medical facility;
a workflow component implemented by a fourth plurality of instructions executed with the at least one hardware processor, the workflow component to:
generate data values to provide electronic worklists associated with respective evaluators, the electronic worklists to list pending diagnostic evaluation tasks designated for performance by the respective evaluators, wherein the data values to provide the electronic worklists are communicated to computing systems of the respective evaluators;
initiate a command to designate a particular evaluator of the respective evaluators to perform the diagnostic evaluation task, wherein the particular evaluator is designated based on a match of at least one qualification of the particular evaluator with at least one requirement of the diagnostic evaluation task, using the parameterized qualification characteristic data values; and
update the electronic worklist for the particular evaluator in response to the command to designate the particular evaluator, wherein the electronic worklist for the particular evaluator is updated to include a pending state for the diagnostic evaluation task; and
a data transmission component implemented by a fifth plurality of instructions executed with the at least one hardware processor, the data transmission component to, under computerized control:
transmit the plurality of digital medical images, via a network, to a computing device associated with the particular evaluator, in response to a command received from the particular evaluator via the electronic worklist to accept the diagnostic evaluation task from the pending state;
wherein the plurality of digital medical images are transmitted and made accessible to the computing device associated with the particular evaluator for performance of the diagnostic evaluation task, based on the acceptance of the diagnostic evaluation task and management of the electronic worklist for the respective evaluators, such that the plurality of digital medical images are not transmitted to the computing systems of the respective evaluators before acceptance of the diagnostic evaluation task.

2. The data processing system of claim 1, further comprising:
an order verification processing component implemented by a sixth plurality of instructions executed with the at least one hardware processor, the order verification processing component to, under computerized control:
electronically transmit the electronic order data to the medical facility that performed the medical imaging procedure for verification of an evaluation order indicated in the electronic order data; and
receive the verification of the electronic order data from the medical facility.

3. The data processing system of claim 2, wherein the electronic imaging data is received in a first HL7-compliant communication, and wherein the electronic order data is transmitted to the medical facility for verification in a second HL7-compliant communication.

4. The data processing system of claim 1, further comprising:
an order population component implemented by a sixth plurality of instructions executed with the at least one hardware processor, the order population component to, under computerized control:
electronically populate at least one field of the electronic order data using at least one data value provided by the electronic imaging data.

5. The data processing system of claim 1, wherein the medical data processing component determines the at least one requirement of the evaluator for the diagnostic evaluation task on a basis of at least one requirement that includes: licensing, credentialing, or specialization of the evaluator.

6. The data processing system of claim 1, wherein the diagnostic evaluation task of the plurality of digital medical images involves a radiological image interpretation, wherein the particular evaluator is a qualified radiologist and wherein the plurality of evaluators includes a plurality of remotely located radiologists, and wherein the workflow component designates the particular evaluator based on a match of characteristics tracked for the particular evaluator with at least one assignment criterion, and wherein the at least one assignment criterion assists the designation of the qualified radiologist from the plurality of remotely located radiologists.

7. The data processing system of claim 6, wherein the workflow component designates the particular evaluator based on a match of characteristic information stored for the particular evaluator with information stored for the at least one assignment criterion, wherein the information stored for the at least one assignment criterion relates to at least one of: connection information for connectivity of the remotely located radiologists, scheduling information for scheduled availability of the remotely located radiologists, forecasting information for projected availability of the remotely located radiologists, preference information of the remotely located radiologists, or preference information of the medical facility providing the electronic imaging data.

8. The data processing system of claim 1, wherein the diagnostic evaluation task of the plurality of digital medical images involves a pathological image examination, wherein the plurality of digital medical images are pathology images, wherein the particular evaluator is a pathologist and wherein the plurality of evaluators includes a plurality of remotely located pathologists, and wherein the diagnostic evaluation task includes a pathological examination of the digital medical images by the pathologist.

9. The data processing system of claim 1, wherein the electronic worklists for the respective evaluators include the electronic worklist for another evaluator from the plurality of evaluators, and wherein the workflow component is additionally to:
    initiate a command to designate the another evaluator to perform the diagnostic evaluation task, wherein the another evaluator is designated based on a match of at least one qualification of the another evaluator with the at least one requirement of the evaluator for the diagnostic evaluation task;
    update the electronic worklist for the another evaluator in response to the command to designate the another evaluator, wherein the electronic worklist for the another evaluator is updated to indicate a pending state for the performance of the diagnostic evaluation task; and
    update the electronic worklist for the another evaluator in response to acceptance of the diagnostic evaluation task by the particular evaluator, wherein the electronic worklist for the another evaluator is updated to remove the pending state for the performance of the diagnostic evaluation task.

10. A non-transitory machine-readable medium including instructions to process medical imaging data, the instructions which when executed by a computing machine cause the computing machine to perform operations that:
    extract data values from a set of electronic imaging data that includes a plurality of digital medical images, the plurality of digital medical images originating from a medical imaging procedure performed by a medical imaging modality at a medical facility;
    extract data values from electronic order data, wherein the electronic order data is associated with the plurality of digital medical images based on data values provided in the electronic imaging data, and wherein the electronic order data specifies characteristics of a diagnostic evaluation task for the plurality of digital medical images;
    generate data values that identify characteristics of the diagnostic evaluation task for the plurality of digital medical images, based on the data values extracted from the electronic order data;
    perform an evaluation of parameterized qualification characteristic data values for a plurality of evaluators to perform the diagnostic evaluation task, using the identified characteristics of the diagnostic evaluation task, the evaluation to apply rules which identify respective evaluators that are credentialed or licensed to perform the diagnostic evaluation task for the medical facility;
    generate data values to provide electronic worklists associated with respective evaluators, the electronic worklists to list pending diagnostic evaluation tasks designated for performance by the respective evaluators, wherein the data values to provide the electronic worklists are communicated to computing systems of the respective evaluators;
    initiate a command to designate a particular evaluator of the respective evaluators to perform the diagnostic evaluation task, wherein the particular evaluator is designated based on a match of at least one qualification of the particular evaluator with at least one requirement of the diagnostic evaluation task, using the parameterized qualification characteristic data values;
    update the electronic worklist for the particular evaluator in response to the command to designate the particular evaluator, wherein the electronic worklist for the particular evaluator is updated to include a pending state for the diagnostic evaluation task; and
    transmit the plurality of digital medical images, via a network, to a computing device associated with the particular evaluator, in response to a command received from the particular evaluator via the electronic worklist to accept the diagnostic evaluation task from the pending state;
    wherein the plurality of digital medical images are transmitted and made accessible to the computing device associated with the particular evaluator for performance of the diagnostic evaluation task, based on the acceptance of the diagnostic evaluation task and management of the electronic worklist for the respective evaluators, such that the plurality of digital medical images are not transmitted to the computing systems of the respective evaluators before acceptance of the diagnostic evaluation task.

11. The machine-readable medium of claim 10, the computing machine to further perform operations that:
    electronically transmit the electronic order data to the medical facility that performed the medical imaging procedure for verification of an evaluation order indicated in the electronic order data, and receive the verification of the evaluation order from the medical facility.

12. The machine-readable medium of claim 10, the computing machine to further perform operations that:
    electronically populate at least one field of the electronic order data using at least one data value provided by the electronic imaging data.

13. The machine-readable medium of claim 10, the computing machine to further perform operations that:
    determine the at least one requirement of the evaluator for the diagnostic evaluation task on a basis of at least one requirement that includes: licensing, credentialing, or specialization of the evaluator.

14. The machine-readable medium of claim 10, the computing machine to further perform operations that:
    designate the particular evaluator based on a match of characteristics tracked for the particular evaluator with at least one assignment criterion, wherein the diagnostic evaluation task of the plurality of digital medical images involves a radiological image interpretation, wherein the particular evaluator is a qualified radiologist and wherein the plurality of evaluators includes a plurality of remotely located radiologists, and wherein the at least one assignment criterion assists the designation of the qualified radiologist from the plurality of remotely located radiologists.

15. The machine-readable medium of claim 10, the computing machine to further perform operations that:
    designate the particular evaluator based on a match of characteristic information stored for the particular evaluator with stored information indicating at least one assignment criterion for a pathology study, wherein the diagnostic evaluation task of the plurality of digital medical images involves a pathological image examination, wherein the plurality of digital medical images are pathology images, wherein the particular evaluator is a pathologist and wherein the plurality of evaluators includes a plurality of remotely located pathologists, and wherein the diagnostic evaluation task includes a pathological examination of the digital medical images by the pathologist.

16. The machine-readable medium of claim 10, wherein the electronic worklists for the respective evaluators include the electronic worklist for another evaluator from the plurality of evaluators, and wherein the instructions cause the computing machine to further perform operations that:

initiate a command to designate the another evaluator to perform the diagnostic evaluation task, wherein the another evaluator is designated based on a match of at least one qualification of the another evaluator with the at least one requirement of the evaluator for the diagnostic evaluation task;

update the electronic worklist for the another evaluator in response to designate the another evaluator, wherein the electronic worklist for the another evaluator is updated to indicate a pending state for the performance of the diagnostic evaluation task; and update the electronic worklist for the another evaluator in response to acceptance of the diagnostic evaluation task by the particular evaluator, wherein the electronic worklist for the another evaluator is updated to remove the pending state for the performance of the diagnostic evaluation task.

17. A method for processing medical data in a workflow through use of a data processing system, the data processing system comprising at least one hardware processor performing electronic operations, the electronic operations including:

extracting data values from a set of electronic imaging data that includes a plurality of digital medical images, the plurality of digital medical images originating from a medical imaging procedure performed by a medical imaging modality at a medical facility;

extracting data values from electronic order data, wherein the electronic order data is associated with the plurality of digital medical images based on data values provided in the electronic imaging data, and wherein the electronic order data specifies characteristics of a diagnostic evaluation task for the plurality of digital medical images;

generating data values that identify characteristics of the diagnostic evaluation task for the plurality of digital medical images, based on the data values extracted from the electronic order data;

performing an evaluation of parameterized qualification characteristic data values for a plurality of evaluators to perform the diagnostic evaluation task, using the identified characteristics of the diagnostic evaluation task, the evaluation to apply rules which identify respective evaluators that are credentialed or licensed to perform the diagnostic evaluation task for the medical facility;

generating data values to provide electronic worklists associated with respective evaluators, the electronic worklists to list pending diagnostic evaluation tasks designated for performance by the respective evaluators, wherein the data values to provide the electronic worklists are communicated to computing systems of the respective evaluators;

initiating a command to designate a particular evaluator of the respective evaluators to perform the diagnostic evaluation task, wherein the particular evaluator is designated based on a match of at least one qualification of the particular evaluator with at least one requirement of the diagnostic evaluation task, using the parameterized qualification characteristic data values;

updating the electronic worklist for the particular evaluator in response the command to designate the particular evaluator, wherein the electronic worklist for the particular evaluator is updated to include a pending state for the diagnostic evaluation task; and transmitting the plurality of digital medical images, via a network, to a computing device associated with the particular evaluator, in response to a command received from the particular evaluator via the electronic worklist to accept the diagnostic evaluation task from the pending state;

wherein the plurality of digital medical images are transmitted and made accessible to the computing device associated with the particular evaluator for performance of the diagnostic evaluation task, based on the acceptance of the diagnostic evaluation task and management of the electronic worklist for the respective evaluators, such that the plurality of digital medical images are not transmitted to the computing systems of the respective evaluators before acceptance of the diagnostic evaluation task.

18. The method of claim 17, further comprising:
electronically transmitting the electronic order data to the medical facility that performed the medical imaging procedure for verification of an evaluation order indicated in the electronic order data, and electronically receiving the verification of the evaluation order from the medical facility.

19. The method of claim 17, further comprising:
electronically populating at least one field of the electronic order data using at least one data value provided by the electronic imaging data.

20. The method of claim 17, wherein the at least one requirement of the evaluator for the diagnostic evaluation task is determined on a basis of at least one requirement that includes: licensing, credentialing, or specialization of the evaluator.

21. The method of claim 17, further comprising:
designating the particular evaluator based on a match of characteristics tracked for the particular evaluator with at least one assignment criterion, wherein the diagnostic evaluation task of the plurality of digital medical images involves a radiological image interpretation, wherein the particular evaluator is a qualified radiologist and wherein the plurality of evaluators includes a plurality of remotely located radiologists, and wherein the at least one assignment criterion assists the designation of the qualified radiologist from the plurality of remotely located radiologists.

22. The method of claim 17, further comprising:
designating the particular evaluator based on a match of characteristic information stored for the particular evaluator with stored information indicating at least one assignment criterion for a pathology study, wherein the diagnostic evaluation task of the plurality of digital medical images involves a pathological image examination, wherein the plurality of digital medical images are pathology images, wherein the particular evaluator is a pathologist and wherein the plurality of evaluators includes a plurality of remotely located pathologists, and wherein the diagnostic evaluation task includes a pathological examination of the digital medical images by the pathologist.

23. The method of claim 17, wherein the electronic worklists for the respective evaluators include the electronic worklist for another evaluator from the plurality of evaluators, and wherein the electronic operations further include:

initiating a command to designate the another evaluator to perform the diagnostic evaluation task, wherein the another evaluator is designated based on a match of at least one qualification of the another evaluator with the at least one requirement of the evaluator for the diagnostic evaluation task;

updating the electronic worklist for the another evaluator in response to designate the another evaluator, wherein the electronic worklist for the another evaluator is updated to indicate a pending state for the performance of the diagnostic evaluation task; and updating the electronic worklist for the another evaluator in response to acceptance of the diagnostic evaluation task by the particular evaluator, wherein the electronic worklist for the another evaluator is updated to remove the pending state for the performance of the diagnostic evaluation task.

* * * * *